(12) United States Patent
Masuda et al.

(10) Patent No.: US 9,545,241 B2
(45) Date of Patent: Jan. 17, 2017

(54) BLOOD VESSEL FUNCTION INSPECTING APPARATUS

(71) Applicants: Hiroshi Masuda, Nagoya (JP); Chikao Harada, Nagoya (JP); Hidenori Suzuki, Nagoya (JP)

(72) Inventors: Hiroshi Masuda, Nagoya (JP); Chikao Harada, Nagoya (JP); Hidenori Suzuki, Nagoya (JP)

(73) Assignee: UNEX CORPORATION, Nagoya-Shi (JP)

( * ) Notice: Subject to any disclaimer, the term of this patent is extended or adjusted under 35 U.S.C. 154(b) by 221 days.

(21) Appl. No.: 14/467,889

(22) Filed: Aug. 25, 2014

(65) Prior Publication Data

US 2014/0364729 A1 Dec. 11, 2014

Related U.S. Application Data

(62) Division of application No. 13/394,496, filed as application No. PCT/JP2009/065767 on Sep. 9, 2009, now Pat. No. 8,845,542.

(51) Int. Cl.
*A61B 5/02* (2006.01)
*A61B 8/08* (2006.01)
(Continued)

(52) U.S. Cl.
CPC ............. *A61B 8/485* (2013.01); *A61B 5/0225* (2013.01); *A61B 5/02035* (2013.01);
(Continued)

(58) Field of Classification Search
None
See application file for complete search history.

(56) References Cited

U.S. PATENT DOCUMENTS 6,113,543 A 9/2000 Bonnefous
2003/0195618 A1* 10/2003 Abraham ................ A61L 27/24
623/1.41
(Continued)

FOREIGN PATENT DOCUMENTS

CA WO 2007140593 A1 * 12/2007 ......... A61B 5/02007
JP A-2000-501327 2/2000
(Continued)

OTHER PUBLICATIONS

Japanese Patent Office, Notification of Reason(s) for Rejection mailed Aug. 26, 2014 in Japanese Patent Application No. 2013-259677 w/English-language Translation.
(Continued)

*Primary Examiner* — Etsub Berhanu
(74) *Attorney, Agent, or Firm* — Oliff PLC

(57) ABSTRACT

It is provided a blood vessel function inspecting apparatus including: a blood vessel diameter measuring portion configured to measure a diameter of a blood vessel; a blood vessel wall thickness measuring portion configured to measure a wall thickness of the blood vessel; and a blood vessel function index value calculating portion configured to calculate a function index value for diagnosing the blood vessel of its function, after releasing of the blood vessel from blood flow obstruction, by dividing an amount of dilatation of said diameter of the blood vessel continuously measured by said blood vessel diameter measuring portion, by the wall thickness measured by said blood vessel wall thickness measuring portion.

6 Claims, 17 Drawing Sheets

(51) Int. Cl.
*A61B 5/022* (2006.01)
*A61B 8/06* (2006.01)
*A61B 8/00* (2006.01)
*A61B 5/0225* (2006.01)
*G01S 15/89* (2006.01)

(52) U.S. Cl.
CPC ............ *A61B 5/02225* (2013.01); *A61B 8/06* (2013.01); *A61B 8/0858* (2013.01); *A61B 8/0891* (2013.01); *A61B 8/4218* (2013.01); *A61B 8/488* (2013.01); *A61B 5/5223* (2013.01); *G01S 15/899* (2013.01)

(56) References Cited

U.S. PATENT DOCUMENTS

| | | | |
|---|---|---|---|
| 2006/0241460 A1 | 10/2006 | Kimura et al. | |
| 2008/0214961 A1 | 9/2008 | Matsumoto et al. | |
| 2008/0300835 A1* | 12/2008 | Hixon ................. | G06F 17/5018 703/2 |
| 2009/0216133 A1 | 8/2009 | Kassab | |
| 2010/0130864 A1 | 5/2010 | Donnelly et al. | |

FOREIGN PATENT DOCUMENTS

| | | | |
|---|---|---|---|
| JP | A-2003-144395 | 5/2003 | |
| JP | A-2006-115979 | 5/2006 | |
| JP | A-2006-166974 | 6/2006 | |
| JP | A-2006-218169 | 8/2006 | |
| JP | A-2007-135894 | 6/2007 | |
| JP | A-2008-061910 | 3/2008 | |
| JP | A-2008-212366 | 9/2008 | |
| JP | A-2009-089911 | 4/2009 | |
| JP | A-2009-538644 | 11/2009 | |
| WO | WO 98/14119 A1 | 4/1998 | |
| WO | WO 2007/014593 A1 | 2/2007 | |
| WO | WO 2007/140593 A1 | 12/2007 | |
| WO | WO 2008127732 A2 * | 10/2008 | ............. A61F 2/062 |
| WO | WO 2009009140 A1 * | 1/2009 | ......... A61B 5/02007 |

OTHER PUBLICATIONS

International Search Report issued in International Application No. PCT/JP2009/065767 dated Dec. 28, 2009.

* cited by examiner

FMD (DILATATION AMOUNT R/BLOOD VESSEL DIAMETER d1 * 100%)

BLOOD VESSEL DIAMETER d1(mm)

BLOOD VESSEL FUNCTION INSPECTING APPARATUS

This is a Divisional of application Ser. No. 13/394,496 filed Mar. 6, 2012, which is a National Stage of Application No. PCT/JP2009/065767 filed Sep. 9, 2009. The prior applications, including the specifications, drawings and abstracts are incorporated herein by reference in their entirety.

TECHNICAL FIELD

The present invention relates to a blood vessel function inspecting medical apparatus, and more particularly to an inspecting apparatus for diagnosing a condition of a blood vessel of its function, on the basis of various kinds of information measured by an ultrasonic sensor, for example.

BACKGROUND ART

As one method of detecting a disease such as arteriosclerosis at an early stage of the disease, a method of diagnosing a blood vessel of its function is drawing a recent attention. Patent Document 1 discloses an example of a blood vessel dynamic characteristic measuring apparatus, which is configured to measure a blood flow velocity distribution within a blood vessel, and to calculate a blood shear rate distribution, a blood viscosity distribution and a blood shear stress on the basis of the measured blood flow velocity distribution. This document proposes the use of the calculated blood viscosity distribution or a blood shear stress distribution as one index value for diagnosing the blood vessel of its function. There is also known a method wherein a diameter of a blood vessel of a subject person at rest (rest-time blood vessel diameter) is measured, and a diameter of the blood vessel is measured after releasing of the blood vessel from blood flow obstruction at a portion of the antebrachium maintained for about five minutes, to calculate a blood vessel diameter increase ratio FMD (blood vessel diameter dilatation amount/rest-time blood vessel diameter*100%) on the basis of an amount of dilatation of the blood vessel diameter after releasing of the blood vessel from the blood flow obstruction, and the rest-time blood vessel diameter, for using this blood vessel diameter increase ratio FMD as the index value for diagnosing the blood vessel of its function. It is also known to use a thickness of the blood vessel wall or a stress acting on the blood vessel wall, as the index value for diagnosing the blood vessel of its function.

PRIOR ART DOCUMENTS

Patent Documents

Patent Document 1: JP-2006-166974 A
Patent Document 2: JP-2003-144395 A

SUMMARY OF THE INVENTION

Object Achieved by the Invention

By the way, none of the above-described various parameters proposed to be used as the index values for diagnosing the blood vessel of its function are confirmed as an optimum index value for diagnosing the blood vessel of its function, so that there is a room for an improvement regarding the index value.

It is an object of this invention to provide a blood vessel function inspecting apparatus for diagnosing a blood vessel of its function, which apparatus permits an improvement of accuracy of diagnosis of the blood vessel function.

Means for Achieving the Object

In view of the above, the present inventors discovered that the blood vessel can be diagnosed of its function more accurately than in the prior art, by using, as a new index value for diagnosing the blood vessel of its function, a value (=blood vessel diameter dilatation amount/blood vessel wall thickness) obtained by dividing an amount of dilatation of the blood vessel of the subject person obtained by continuously measuring the diameter of the blood vessel that dilates after releasing the blood flow obstruction, by the wall thickness of the blood vessel. By processing measurement data with respect to the above-indicated new index value and an index value (=blood vessel diameter wall thickness/blood vessel diameter) obtained by dividing the blood vessel wall thickness by the blood vessel diameter, the inventors discovered that the new index value (=blood vessel dilatation amount/blood vessel wall thickness) decreases with an increase of the index value (=blood vessel wall thickness/blood vessel diameter). Further, the inventors discovered that the accuracy of diagnosis of the blood vessel function can be improved, by processing the measurement data with respect to the blood shear stress and the blood wall stress.

Namely, the object indicated above is achieved according to the principle of the invention, which provides a blood vessel function inspecting apparatus characterized by comprising (a) a blood vessel diameter measuring portion configured to measure a diameter of a blood vessel, (b) a blood vessel wall thickness measuring portion configured to measure a wall thickness of the blood vessel, and (c) a blood vessel function index value calculating portion configured to calculate a function index value for diagnosing the blood vessel for its function, after releasing of the blood vessel from blood flow obstruction, by dividing an amount of dilatation of the above-described diameter of the blood vessel continuously measured by the above-described blood vessel diameter measuring portion, by the wall thickness measured by the above-described blood vessel wall thickness measuring portion.

Advantages of the Invention

According to the present invention described above, the function index value (dilatation amount/wall thickness) for diagnosing the blood vessel of its function is calculated after releasing of the blood vessel from the blood flow obstruction, by dividing the dilatation amount of the blood vessel diameter continuously measured by the above-described blood vessel diameter measuring portion, by the wall thickness measured by the above-described blood vessel wall thickness measuring portion, so that the blood vessel can be diagnosed of its function with a higher degree of accuracy than in the prior art. For instance, the prior art uses an index value (FMD value: dilatation amount/blood vessel diameter*100%) obtained by dividing the above-described dilatation amount of the blood vessel after releasing of the blood vessel from the blood flow obstruction, by the blood vessel diameter, for diagnosing the blood vessel of its function on the basis of the thus obtained index value. Since the amount of change of the function index value according to the invention with a change of the function of the blood vessel is larger than that of the prior art index value (FMD value)

in addition to having correlation with the prior art index value, the diagnosis of the blood vessel function can be implemented more adequately on the basis of the function index value according to the invention. Namely, the function index value according to the invention more accurately reflects a change of the blood vessel function than the prior art index value, since the amount of change of the wall thickness is larger than the amount of change of the blood vessel diameter.

Preferably, the above-described blood vessel function index value calculating portion is further configured to calculate an organic index value, by dividing the above-described wall thickness by the diameter of the blood vessel, so that the blood vessel is diagnosed of its function on the basis of a relationship between the above-described function index value and the above-described organic index value. In this case, the function index value tends to decrease with an increase of the organic index value, so that the diagnosis of the blood vessel function can be implemented more accurately on the basis of the above-indicated tendency. For instance, the blood vessel function can be diagnosed for any abnormality, on the basis of a direction and a degree of deviation of the measurement data from the above-indicated tendency.

Also preferably, the blood vessel function index value calculating portion is further configured to calculate a function/organic index value, by dividing the above-described function index value by the above-described organic index value, so that the blood vessel is diagnosed of its function on the basis of the above-described function/organic index value. In this case, the measurement data processed with respect to the above-described function/organic index value have a reduced degree of variation, permitting an improved accuracy of diagnosis of the blood vessel function.

Also preferably, each of the above-described index values is standardized by the shear stress, so that each index value is compensated by the shear stress, so as to reduce a degree of variation of the measurement data, for further improving the accuracy of diagnosis of the blood vessel function. That is, the variation of the index value due to a difference of the shear stress is eliminated to further improve the accuracy of evaluation on the basis of the index value.

Preferably, the object indicated above is achieved according to another aspect of this invention, which provides a blood vessel function inspecting apparatus characterized by comprising (a) a shear stress calculating portion configured to calculate a shear stress, (b) a wall stress calculating portion configured to calculate a wall stress, and (c) a blood vessel function diagnosing portion configured to diagnose a blood vessel of its abnormality of function, depending upon whether at least one of the calculated shear stress and wall stress is outside a corresponding one of optimum ranges respectively predetermined for the above-described shear stress and the above-described wall stress.

As described above, the present blood vessel function inspecting apparatus is provided with the blood vessel function diagnosing portion configured to diagnose the blood vessel of its abnormality of function, depending upon whether at least one of the calculated shear stress and wall stress is outside the corresponding one of the optimum ranges respectively predetermined for the shear stress and the wall stress. Thus, the blood vessel function can be easily diagnosed for any abnormality, by calculating the shear stress and the wall stress. The blood vessel has a compensating function to always hold the shear stress and the wall stress within the optimum ranges, irrespective of variations of the blood flow and blood pressure. If the wall stress increases with a rise of the blood pressure, for example, the wall thickness of the blood vessel increases to hold the wall stress constant. If the shear stress increases with an increase of the blood viscosity, for example, the blood vessel diameter increases to reduce the shear rate for holding the shear stress constant. Thus, the shear stress and wall stress are kept normal owing to the compensating function of the blood vessel. If this compensating function is lost, the shear stress and wall stress deviate from the above-indicated optimum ranges. Accordingly, the diagnosis as to whether the above-indicated compensating function of the blood vessel is normal can be accurately implemented by determining from time to time whether the calculated shear stress and wall stress have deviated from the optimum ranges. If at least one of the shear stress and wall stress is outside the optimum range, for instance, a chronological change of the deviation from the optimum range is monitored from time to time, to synthetically find a cause and an adequate remedy for the deviation, and also an effect of the remedy.

Also preferably, the blood vessel function inspecting apparatus is provided with a display device configured to display a relationship between the calculated shear stress and wall stress, in a two-dimensional graph, and the display device displays a region in which the above-described optimum ranges of the above-described shear stress and wall stress overlap each other, and indicates a position of a calculated result indicative of the relationship between the calculated shear stress and wall stress relative to the above-described region. Since the position of the point indicative of the relationship between the shear stress and the wall stress relative to the region is displayed, the diagnosis as to whether the blood vessel function is normal or not can be easily implemented on the basis of the relative position between the calculated result and the region. Described more specifically, the blood vessel function can be easily diagnosed to be normal if the calculated result is held within the region, and to be abnormal if the calculated result is outside the region.

Also preferably, the blood vessel function inspecting apparatus further comprises a memory portion for storing the shear stress calculated by the above-described shear stress calculating portion, and the wall stress calculated by the above-described wall stress calculating portion successively, and wherein the above-described display device indicates results of present calculation of the above-described shear stress and wall stress, together with results of past calculation of the above-described shear stress and wall stress stored in the above-described memory portion, such that the results of the present calculation are distinguishable from the results of the past calculation. Thus, it is possible to compare the results of the present calculation with the results of the past calculation, and to check a chronological change of the blood vessel function. Accordingly, if one of the shear stress and the wall stress has deviated from the optimum range, the adequate remedy for the deviation and the effect of the remedy can be evaluated depending upon whether the shear stress or wall stress is changing in a direction toward the optimum range.

Also preferably, the above-described shear stress is one of: an integral value of the above-described shear stress within a predetermined period of time preceding a reference point of time which is prior to a present point of time by a predetermined length of time corresponding to a delay of a response of a change of the above-described wall stress which takes place with a change of the above-described shear stress; a mean value of the shear stress per one heart beat pulse within the above-described predetermined period of time; and an integral or mean value of instantaneous values of the shear stress measured in synchronization with the respective heart beat pulses within the above-described predetermined period of time. It is generally known that the endothelial skin of the blood vessel instantaneously responds to a change of the blood flow, but there exists a response time delay from the moment of production of nitrogen monoxide NO to the moment at which the smooth muscles are relaxed due to exposure to the nitrogen monoxide NO which has diffused through the inner layer and reached the smooth muscles. That is, a time delay occurs between the change of the shear stress and the change of the wall stress. In view of this response time delay, the representative value of the shear stress used for the diagnosis of the blood vessel function is calculated on the basis of the shear stress values at the respective points of measurement within the predetermined period of time preceding the reference point of time which is prior to the present point of time of calculation of the wall stress by the length of time corresponding to the response time delay, so that the blood vessel can be diagnosed of its function on the basis of the shear stress and wall stress which have a correlation with each other. It is also noted that the representative value of the shear stress used for the diagnosis of the blood vessel function is not an instantaneous value at a given point of time (e.g., at the reference point of time), but is calculated on the basis of the values of the shear stress at the respective points of time within the predetermined period of time which terminates at the reference point of time, so that the blood vessel can be diagnosed of its function on the basis of the shear stress which reflects the stimuli regularly acting on the blood vessel wall.

Also preferably, the above-described shear stress is calculated on the basis of the blood flow velocity distribution and according to the stored two-dimensional or three-dimensional Navier-Stokes equations. Accordingly, the shear stress is accurately calculated so that the blood vessel function inspecting apparatus is practically operable.

Also preferably, the wall stress is calculated on the basis of a blood pressure, a blood vessel diameter and a wall thickness of the blood vessel. Accordingly, the wall stress is accurately calculated by measuring the above-described blood pressure, the blood vessel diameter and the wall thickness, so that the blood vessel function inspecting apparatus is practically operable.

A preferable form of a blood vessel function inspecting apparatus comprises (a) a shear stress calculating portion configured to calculate a shear stress, (b) a wall stress calculating portion configured to calculate a wall stress, and (c) a display device configured to display a relationship between the calculated shear stress and wall stress, in a two-dimensional graph, (d) the display device displaying a region in which the above-described optimum ranges of the above-described shear stress and wall stress overlap each other, and (e) the display device indicating a position of a calculated result indicative of the relationship between the calculated shear stress and wall stress relative to the above-described region. Since the position of the calculated relationship between the shear stress and the wall stress relative to the region is displayed, the diagnosis as to whether the blood vessel function is normal or not can be easily implemented on the basis of the relative position between the above-indicated point and the region. Described more specifically, the blood vessel function can be easily diagnosed to be normal if the point is held within the region, and to be abnormal if the point is outside the region.

Another preferred form of a blood vessel function inspecting apparatus comprises (a) an ultrasonic probe which irradiates ultrasonic waves toward the above-described blood vessel and which is provided with a longitudinal ultrasonic detector array having a plurality of ultrasonic oscillators arranged linearly in a longitudinal direction of the above-described blood vessel, and a transverse ultrasonic detector array which has a plurality of ultrasonic oscillators arranged linearly in a direction perpendicular to the longitudinal direction of the above-described blood vessel, and (b) wherein a blood flow velocity within the above-described blood vessel is measured with the ultrasonic waves irradiated from the above-described longitudinal ultrasonic detector array, and the above-described blood vessel diameter and blood vessel wall thickness are measured with the ultrasonic waves irradiated from the transverse ultrasonic detector array. Accordingly, it is possible to implement the measurement of the above-described blood flow velocity, the measurement of the above-described blood vessel diameter, and the measurement of the above-described blood vessel wall thickness, concurrently with each other, by using the practically operable ultrasonic probe. For example, the concurrent measurements of the above-described blood flow velocity, blood vessel diameter and wall thickness of the blood vessel can be implemented by alternately operating the above-described longitudinal ultrasonic detector array and the above-described transverse ultrasonic detector array, with an extremely short cycle time.

A further preferable form of a blood vessel function inspecting apparatus comprises (a) an ultrasonic probe which irradiates ultrasonic waves toward the above-described blood vessel and which is provided with a longitudinal ultrasonic detector array having a plurality of ultrasonic oscillators arranged linearly in a longitudinal direction of the above-described blood vessel, and (b) operations of the above-described longitudinal ultrasonic detector array to measure a blood flow velocity within the above-described blood vessel, the above-described blood vessel diameter and the above-described blood vessel wall thickness are alternately performed in time. In this case, it is possible to implement the measurement of the above-described blood flow velocity, the measurement of the above-descried blood vessel diameter and the measurement of the above-described blood vessel wall thickness, concurrently with each other, by using the ultrasonic probe practically used in the art. For example, the concurrent measurements of the above-described blood flow velocity, blood vessel diameter and blood vessel wall thickness can be implemented by operating the above-described longitudinal ultrasonic detector array, with an extremely short cycle time.

MODE FOR CARRYING OUT THE INVENTION

Embodiments of the present invention will be described in detail by reference to the drawings. It is to be understood that the drawings showing the embodiments are simplified or transformed as needed, and do not necessarily accurately indicate the dimensions and shapes of individual elements of the embodiments.

Embodiment 1

Figure 1:
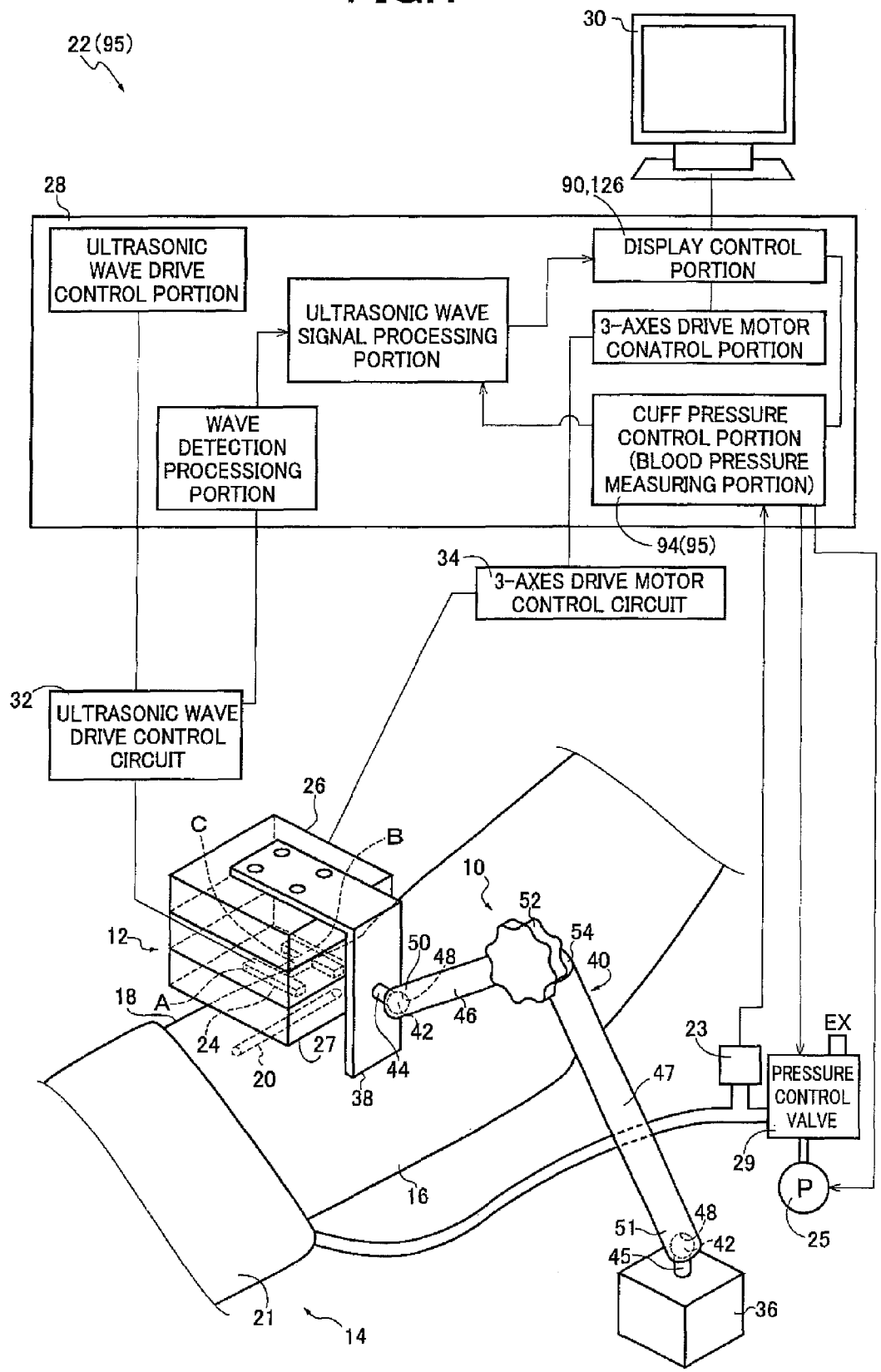
FIG. 1 is a view showing an overall arrangement of a blood vessel function inspecting apparatus according to one embodiment of this invention.

FIG. 1 is the view showing an overall arrangement of a blood vessel function inspecting apparatus 22 constructed to measure a blood flow velocity distribution within a blood vessel 20 immediately below a skin 18 of a brachium 16 of a live body 14, and a diameter and wall thickness of the blood vessel 20 by using a hybrid probe unit 12 held by a sensor holder 10, and to measure a blood pressure by using a cuff 21.

The hybrid probe unit 12, which functions as a sensor for detecting vital body information relating to the blood vessel 20, that is, blood vessel parameters, is provided with an H-type ultrasonic probe 24, and a multi-axes drive device (positioning device) 26 for positioning the ultrasonic probe 24. The ultrasonic probe 24 has a pair of mutually parallel detector arrays consisting of a first short-axis ultrasonic detector array A and a second short-axis ultrasonic detector array B, and a long-axis ultrasonic detector array C which connects the first and second short-axis ultrasonic detector arrays A and B at longitudinally intermediate portions thereof. The ultrasonic detector arrays A, B and C lie on one plane, namely, on a flat detection plane 27. Each of the first short-axis ultrasonic detector array A, second short-axis ultrasonic detector array B, and long-axis ultrasonic detector array C is an elongate member having a multiplicity of ultrasonic oscillators (vibrators) $a_1$-$a_n$ which are formed of a piezoelectric ceramic material and which are arranged linearly.

Figure 2:
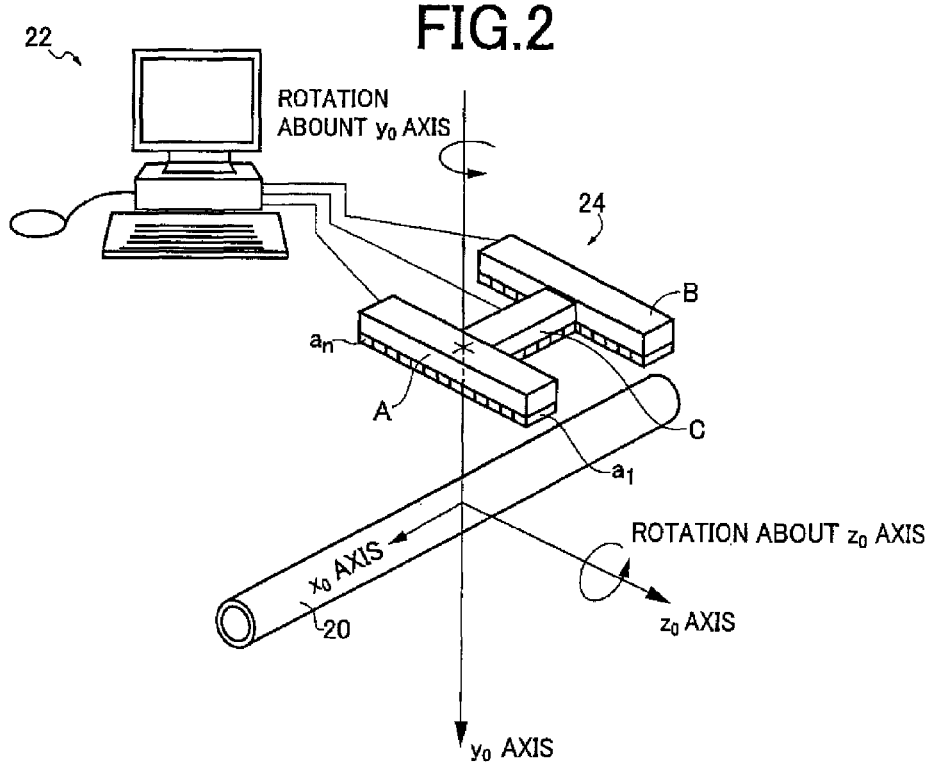
FIG. 2 is a view for explaining rectangular coordinate axes x, y and z for indicating an attitude of an ultrasonic probe used by the blood vessel function inspecting apparatus of FIG. 1, with respect to the blood vessel.

FIG. 2 is the view for explaining $x_0$, $y_0$ and $z_0$ axes of a rectangular coordinate system used in the present embodiment. The axis $z_0$ is parallel to the longitudinal direction of the first short-axis ultrasonic detector array A, and located right below the first short-axis ultrasonic detector array A, and passes a vertical position of the blood vessel 20 or a point vertically close to that vertical position. The $x_0$ axis is parallel to the longitudinal direction of the long-axis ultrasonic detector array C, and is perpendicular to the $z_0$ axis, while the $y_0$ axis passes a point of intersection between the longitudinal direction of the first short-axis ultrasonic detector array A and the longitudinal direction of the long-axis ultrasonic detector array C, and is perpendicular to the above-described $x_0$ and $z_0$ axes. The ultrasonic probe 24 is translated along the $z_0$ axis and rotated about the $y_0$ and $z_0$ axes by the multi-axes drive device 26.

Figure 3:
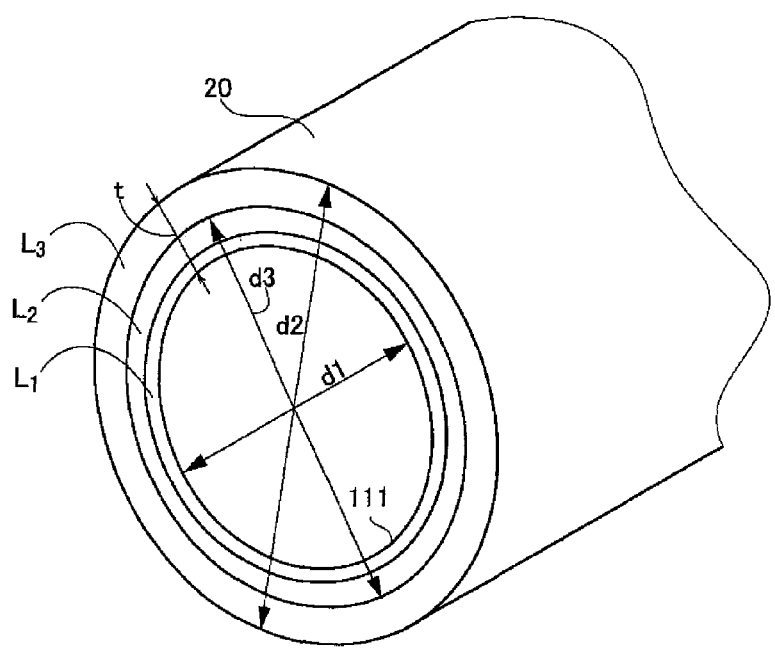
FIG. 3 is an enlarged view for explaining a multi-layered structure of the blood vessel which is a subject irradiated with an ultrasonic wave generated by the ultrasonic probe of FIG. 2.

As shown in FIG. 3, the blood vessel 20 which is a arterial vessel of the brachium, for instance, has a three-layered structure consisting of an inner layer $L_1$, an intermediate layer $L_2$ and an outer layer $L_3$. Since the reflection of an ultrasonic wave takes place in boundary portions having different values of acoustic impedance, a boundary surface between the blood in the lumen of the blood vessel and the inner layer $L_1$, and a boundary surface between the intermediate layer $L_2$ and the outer layer $L_3$ are displayed as white regions, and the tissue is displayed by white and black spots. Further, the boundary surface between the blood and the inner layer $L_1$ is displayed in an image, and a diameter of the inner layer $L_1$ at the boundary surface is measured as a diameter d1 of the blood vessel.

Referring back to FIG. 1, the blood vessel function inspecting apparatus 22 is provided with an electronic control device 28, a monitoring image display device (image display device) 30, an ultrasonic wave drive control circuit 32, and a 3-axes drive motor control circuit 34. The electronic control device 28 is constituted by a so-called microcomputer having a CPU operable to process input signals according to programs stored in a ROM, while utilizing a temporary data storage function of a RAM. The above-described electronic control device 28 is configured to command the ultrasonic wave drive control circuit 32 to apply drive signals to the first short-axis ultrasonic detector array A, second short-axis ultrasonic detector array B and long-axis ultrasonic detector array C of the ultrasonic probe 24 of the hybrid probe unit 12, for irradiating ultrasonic waves. The irradiated ultrasonic waves are reflected as reflected ultrasonic signals, which are detected by the first and second short-axis ultrasonic detector arrays A, B and long-axis ultrasonic detector array C. The reflected ultrasonic signals are processed to generate ultrasonic images of a tissue under the skin 18 in ultrasonic signal processing portion, so that the ultrasonic images can be displayed on the monitoring image display device 30. The electronic control device 28 has functions to measure the blood vessel diameter d1, a wall thickness t of the blood vessel 20 and a blood flow velocity distribution DS, as described below, on the basis of the reflected ultrasonic signals received by its ultrasonic wave signal processing portion, to calculate index values used for diagnosing the blood vessel of its function, as described below, and to diagnose the blood vessel of its function based on the index values.

The monitoring image display device 30 is configured to be able to display the ultrasonic image obtained by the first short-axis ultrasonic detector array A, the ultrasonic image obtained by the second short-axis ultrasonic detector array B, and the ultrasonic image obtained by the long-axis ultrasonic detector array C, in respective image display regions. These image display regions have a common vertical axis along which a depth dimension from the skin 18 is indicated.

The monitoring image display device 30 is further configured to chronologically display an amount of change of the blood vessel diameter d1 from a value during the blood flow obstruction to a value after releasing of the blood vessel from the blood flow obstruction, namely, to display a chronological change of a dilatation amount R of the blood vessel diameter d1, upon evaluation of flow mediated vasodilation.

Upon the above-described evaluation of the flow mediated vasodilation, and generation of the ultrasonic images of the blood vessel 20, the ultrasonic probe 24 is positioned in a predetermined measuring position with respect to the blood vessel 20, by the multi-axes drive device 26 which is operated according to the drive signals received from the 3-axes drive motor control circuit 34 under the control of the electronic control device 28. In the predetermined measuring position, the first short-axis ultrasonic detector array A and the second short-axis ultrasonic detector array B are perpendicular to the blood vessel 20, while the long-axis ultrasonic detector array C is parallel to the blood vessel 20.

The sensor holder 10 is constructed to hold the hybrid probe unit 12 so as to have a predetermined attitude in a predetermined position in a three-dimensional space, that is, in the above-described predetermined measuring position, such that the hybrid probe unit 12 is held in contact with the skin 18 of the brachium 16 of the live body 14, with a low pressure not to cause deformation of the blood vessel 20 immediately below the skin 18. Between the end surface of the ultrasonic probe 24 of the hybrid probe unit 12 and the skin 18, there is usually interposed a well known coupling agent such as jelly, to reduce attenuation of the ultrasonic wave, and reflection and scattering of the ultrasonic wave at the boundary surfaces, for thereby obtaining clear ultrasonic images. This jelly is a gel-like water absorptive high molecular material which has a high content of aqueous components such as agar, and a sufficiently higher degree of natural impedance (sound velocity×density) than air, making it possible to reduce the attenuation of transmitted and received ultrasonic wave signals. The jelly may be replaced by a resin bag charged with water, an olive oil, or glycerin.

The above-described sensor holder 10 is provided with a magnet stand 36, unit fixture 38, connecting members 44, 45, and a universal arm 40. The magnet stand 36 is fixed with a magnetic attraction force, for example, to a desk or a pedestal, and the above-described hybrid probe unit 12 is fixed to the unit fixture 38. The connecting members 44, 45 are fixed at one end thereof to the magnet stand 36 and the unit fixture 38, respectively, and have spherical distal end portions 42. The universal arm 40 connects the magnet stand 36 and the unit fixture 38 to each other through the connecting members 44, 45 and supports the magnet stand 36 and unit fixture 38, such that the magnet stand 36 and the unit fixture 38 are movable relative to each other. The universal arm 40 has two links 46, 47 pivotably connected to each other, universal joint portions 50, 51 having respective engaging holes 48, and a pivotal joint portion 54. The engaging hole 48 is formed in one end portion of each of the two links 46, 47, and the above-described spherical distal end portion 42 is universally fitted in the engaging hole 48, with a predetermined force of resistance to universal motions of the links 46, 47 relative to the spherical distal end portion 42. The two links 46, 47 are pivotably connected to each other at the other end portions by the pivotal joint portion 54, which has a fixing knob 52 provided with an externally threaded portion screwed in tapped holes formed through the above-indicated other end portions of the links 46, 47, so that pivotal motions of the two links 46, 47 are prevented when the fixing knob 52 is tightened.

The multi-axes drive device 26 consists of a $z_0$-axis rotating (yawing) mechanism fixed to the unit fixture 38 and having a $z_0$-axis rotating actuator to rotate the ultrasonic probe 24 about the $z_0$ axis for rotational positioning about $z_0$-axis, a $z_0$-axis translating mechanism having a $z_0$-axis translating actuator to translate the ultrasonic probe 24 along the $z_0$ axis for positioning in a direction parallel to $z_0$-axis, and a $y_0$-axis rotating mechanism having a $y_0$-axis rotating actuator to rotate the ultrasonic probe 24 about the $y_0$ axis for rotational positioning about $y_0$-axis.

The ultrasonic wave drive control circuit 32 shown in FIG. 1 is commanded by the electronic control device 28 to drive the multiplicity of linearly arranged ultrasonic oscillators (vibrators) $a_1$-$a_n$ of the above-described first short-axis ultrasonic detector array A, for example, such that a group of a predetermined number of the ultrasonic oscillators, for example, a group of the 15 ultrasonic oscillators—$a_{15}$, including an ultrasonic oscillator $a_1$ located at the end, are concurrently driven at a frequency of about 10 MHz, with a predetermined phase difference, to implement a beam forming operation to successively irradiate ultrasonic wave beams toward the blood vessel 20, such that the ultrasonic wave beams converge in the direction of arrangement of the ultrasonic oscillators. The ultrasonic wave beams are irradiated with the members of the group of the predetermined number of the ultrasonic oscillators being shifted by one oscillator per each beam forming operation, and the thus irradiated ultrasonic wave beams are scanned to detect reflected waves, which are input to the electronic control device 28.

The electronic control device 28 is configured to synthesize an image on the basis of the above-described reflected waves, that is, a transverse cross sectional image (short-axis image) or a longitudinal cross sectional image (long-axis image) of the blood vessel 20 below the skin 18, and display the image on the monitoring image display device (image display device) 30. Further, the electronic control device 28 is configured to measure, on the basis of the image, an outer layer diameter d2 which is a diameter of the outer layer $L_3$ of the blood vessel 20, or the blood vessel diameter (endothelial skin diameter) d1 which is a diameter of an endothelial skin 111. In addition, the electronic control device 28 is configured to make the blood flow obstruction using cuff 21 for evaluating endothelial skin of the blood vessel and continuously measure the dilatation amount (changing amount) R (=d1−da) of the blood vessel diameter d1 of the blood vessel 20 after releasing of the blood vessel from the blood flow obstruction ("da" representing the blood vessel diameter d1 at rest). The blood flow obstruction is maintained for a predetermined length of time (about five minutes, for instance) while the subject person is at rest, and the blood vessel diameter d1 in the dilatation of the blood vessel due to reactive congestion is measured during a predetermined length of time (about 120 seconds, for instance) after releasing of the blood vessel from the blood flow obstruction.

Figure 4:
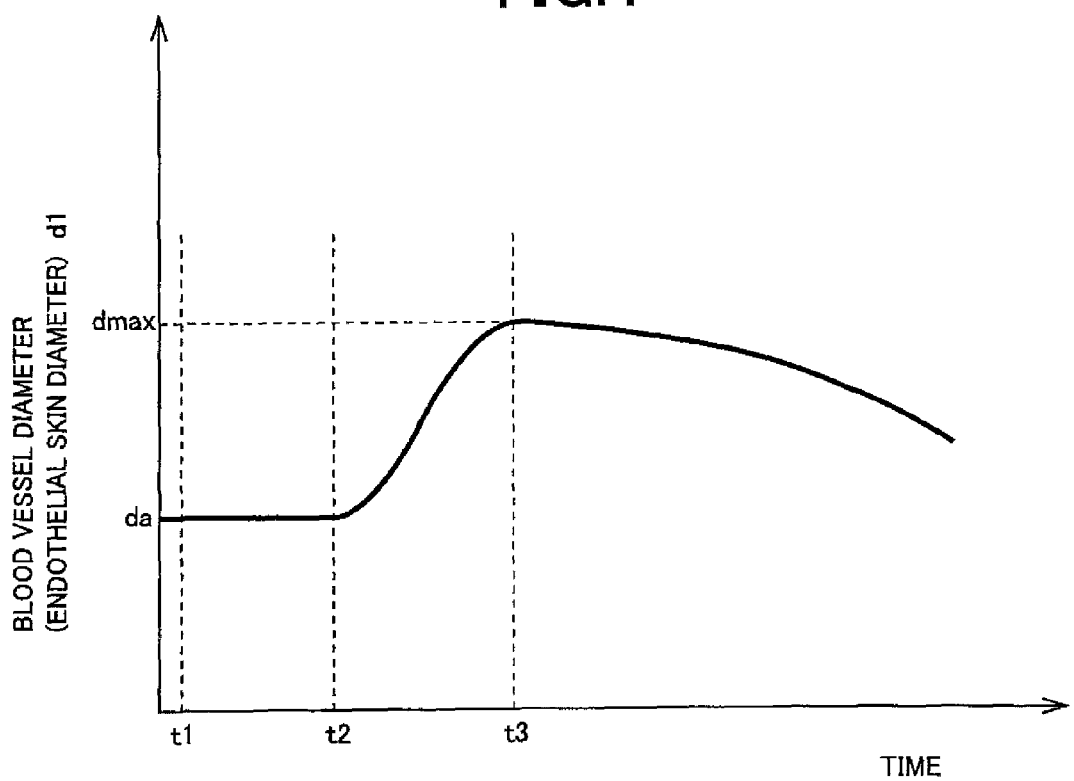
FIG. 4 is a time chart indicating an example of a change of blood vessel diameter (an inside diameter of the blood vessel lumen) after releasing of the blood vessel from blood flow obstruction, which is measured with the ultrasonic wave generated from the ultrasonic probe of FIG. 2.

FIG. 4 is the time chart indicating an example of a change of the blood vessel diameter (endothelial skin diameter) d1 after releasing of the blood vessel from blood flow obstruction. In the example of FIG. 4, the blood vessel is released from blood flow obstruction, at a point of time t1, and the blood vessel diameter d1 begins to increase at a point of time t2, and reaches a maximum value dmax at a point of time t3. Thus, the dilatation amount R of the blood vessel diameter d1 calculated by the electronic control device 28 is maximized at the point of time t3.

The electronic control device 28 is further configured to calculate a wall thickness t (=(d2−d1)/2) of the blood vessel 20 on the basis of the measured outer layer diameter d2 and endothelial skin diameter d1.

Figure 5:
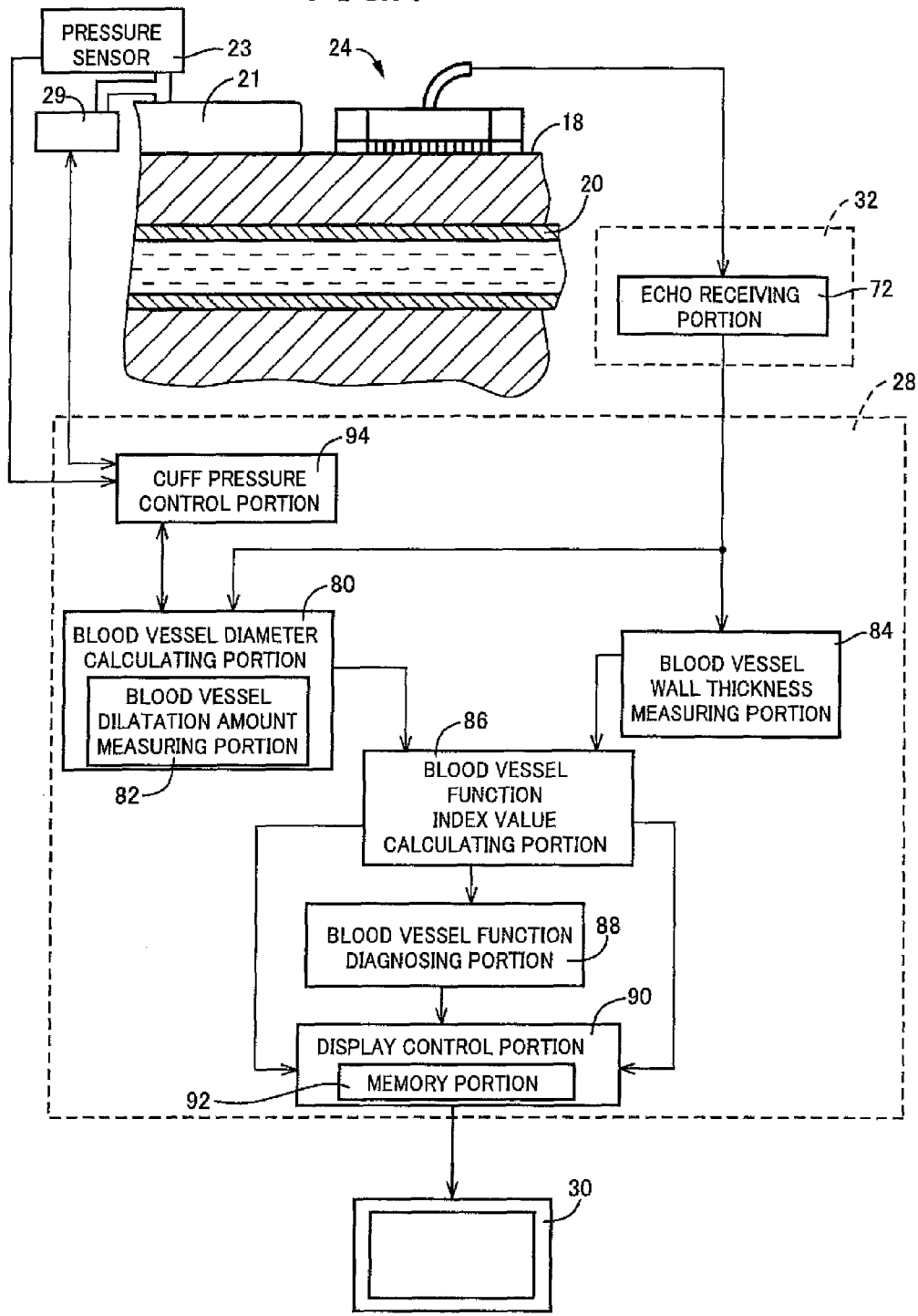
FIG. 5 is a functional block diagram for explaining major control functions of the blood vessel function inspecting apparatus of FIG. 1.

FIG. 5 is the functional block diagram for explaining major control functions of the blood vessel function inspecting apparatus 22. As shown in FIG. 5, the ultrasonic wave drive control circuit 32 is provided with an echo receiving portion in the form of an echo receiving portion 72, and the electronic control device 28 is provided with: a blood vessel diameter measuring portion 80 configured to measure the blood vessel diameter d1; a blood vessel wall thickness measuring portion 84 configured to measure the wall thickness t of the blood vessel 20; a blood vessel dilatation amount measuring portion 82 configured to continuously measure an amount of change (amount of dilatation) of the blood vessel diameter d1 after releasing of the blood vessel from the blood flow obstruction; a blood vessel function index value calculating portion 86 configured to calculate an index value for implementing a diagnosis of the blood vessel function as described below; a blood vessel function diagnosing portion 88 configured to implement the diagnosis of the blood vessel function on the basis of the index value calculated by the blood vessel function index value calculating portion 86; a display control portion in the form of a display control portion 90; and a cuff pressure control portion 94 (blood pressure measuring portion 94) configured to control the blood flow obstruction of the blood vessel 20.

The echo receiving portion 72 is configured to receive the reflected waves of the ultrasonic beams generated from the ultrasonic probe 24, and supply the reflected waves to the electronic control device 28. For example, the echo receiving portion 72 receives the reflected waves of the ultrasonic beam generated from the first short-axis ultrasonic detector array A, and supplies the reflected waves to the blood vessel diameter measuring portion 80 and the blood vessel wall thickness measuring portion 84.

The blood vessel diameter measuring portion 80 is configured to synthesize the blood vessel image on the basis of the reflected waves of the ultrasonic beams from the first short-axis ultrasonic detector array A, which reflected waves have been supplied from the echo receiving portion 72. On the basis of the synthesized blood vessel image, the blood vessel diameter measuring portion 80 measures the outer layer diameter d2 of the blood vessel 20 under the skin 18 shown in FIG. 3, and the blood vessel diameter (diameter of the endothelial skin 111) d1.

The blood vessel diameter measuring portion 80 is configured to continuously measure the blood vessel diameter d1 which changes, as shown in FIG. 4, due to dilatation of the blood vessel 20 after releasing from the blood flow obstruction by the cuff 21, which is maintained for the predetermined length of time (about five minutes, for example). The blood vessel dilatation amount measuring portion 82 is configured to measure an amount of change of the diameter d1 of the blood vessel 20 measured after releasing of the blood vessel 20 from the blood flow obstruction, more specifically, the dilatation amount R (=d1−da) of the blood vessel diameter d1 ("da" representing the blood vessel diameter d1 at rest). In this connection, it is noted that the blood flow obstruction of the blood vessel 20 is controlled by the cuff pressure control portion 94, by controlling the pressure of the cuff 21 with a pressure control valve 29. Described more specifically, the pressure control valve 29 is controlled to keep the pressure within the cuff 21 at a value high enough to almost stop the blood flow through the blood vessel 20 during the blood flow obstruction, and to instantaneously evacuate the cuff 21 during releasing the blood flow obstruction.

The blood vessel wall thickness measuring portion 84 is configured to synthesize the blood vessel image on the basis of the reflected waves of the ultrasonic beams from the first short-axis ultrasonic detector array A, which reflected waves have been supplied from the echo receiving portion 72. The blood vessel wall thickness measuring portion 84 measures the wall thickness t of the blood vessel 20 under the skin 18 shown in FIG. 3, on the basis of the outer layer diameter d2 of the blood vessel 20 and blood vessel diameter (diameter of the endothelial skin 111) d1 which have been measured on the basis of the synthesized blood vessel image. It is noted that the wall thickness t of the blood vessel 20 is calculated as a difference t (=(d2−d1)/2) between the outer layer diameter d2 and the endothelial skin diameter d1 shown in FIG. 3. The blood vessel wall thickness measuring portion 84 may be configured to continuously measure the wall thickness t, like the blood vessel diameter measuring portion 80, or to measure the wall thickness t at a predetermined point of time.

The blood vessel function index value calculating portion 86 is configured, for example, to divide the dilatation amount R of the diameter d1 of the blood vessel 20 measured by the blood vessel diameter measuring portion 80 after releasing of the blood vessel 20 from the blood flow obstruction, by the wall thickness t measured by the blood vessel wall thickness measuring portion 84, to obtain a function index value X1 (=dilatation amount R/wall thickness t) for implementing the diagnosis of the blood vessel function. The function index value X1 is calculated on the basis of a representative value of the dilatation amount R and a representative value of the wall thickness t, for instance, on the basis of the maximum value Rmax (=dmax−da) of the dilatation amount R after releasing of the blood vessel from the blood flow obstruction, and the value of the wall thickness t at the point of time at which the dilatation amount R of the blood vessel 20 has the maximum value Rmax.

Figure 6:
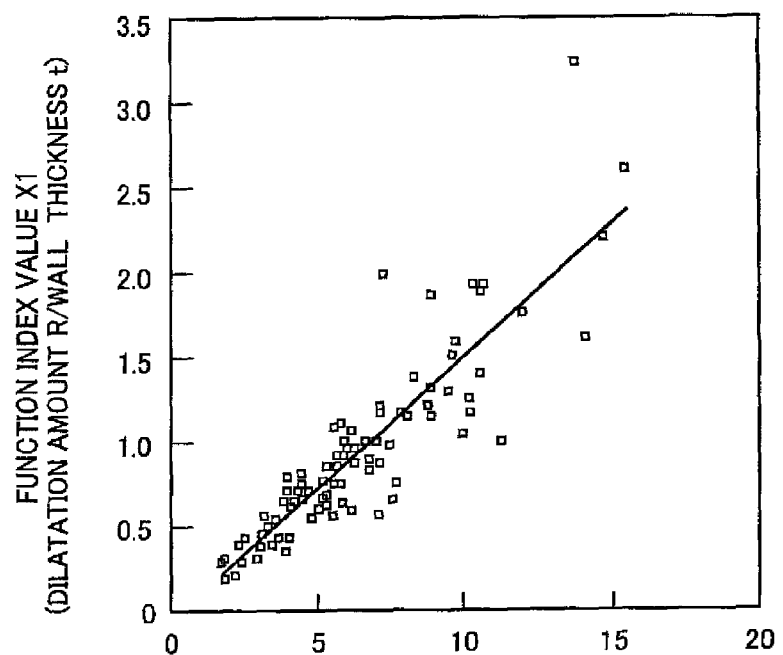
FIG. 6 is a graph indicating a relationship between a value (function index value) obtained by dividing a blood vessel dilatation amount measured by the blood vessel function inspecting apparatus by a blood vessel wall thickness, and a known FMD value (dilatation amount/rest-time blood vessel diameter*100%)

FIG. 6 is the graph indicating a relationship between the function index value X1 obtained by dividing the dilatation amount R of the of the blood vessel 20 by the wall thickness t, and a known FMD value (dilatation amount R/rest-time blood vessel diameter da*100%). As shown in FIG. 6, the function index value X1 (=dilatation amount R/wall thickness t) and the FMD are correlated with each other. It is noted that the blood vessel diameter d1 increases as a result of relaxation of smooth muscles due to production of nitrogen monoxide (NO) upon the FMD evaluation, and that the nitrogen monoxide (NO) produced within endothelial skin cells of the blood vessel 20 diffuses through the inner layer and reaches the smooth muscles. Therefore, the wall thickness t is considered as one of factors which determine the diffusion time of the nitrogen monoxide. The wall thickness t is also considered as one of factors which determine a mass of the smooth muscles that is responsive to the nitrogen monoxide (NO). Therefore, the function index value X1 and the FMD value are considered to be correlated with each other. Accordingly, the function index value X1 may be used as an index value alternative to the known FMD value described above.

Figure 7:
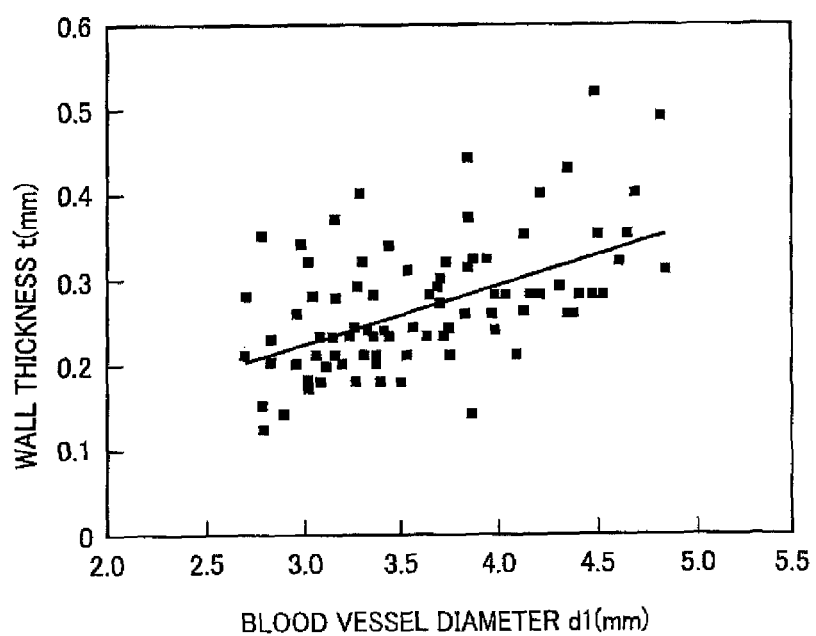
FIG. 7 is a graph indicating a relationship between the blood vessel wall thickness and the blood vessel diameter measured by the blood vessel function inspecting apparatus.

The blood vessel function index value calculating portion 86 is further configured to divide the wall thickness t by the blood vessel diameter d1 to obtain an organic index value X2 (wall thickness t/blood vessel diameter d1) for implementing the diagnosis of the blood vessel function. The organic index value X2 is calculated on the basis of a representative value of the blood vessel diameter d1 and a representative value of the wall thickness t, for instance, on the basis of the maximum value dmax of the blood vessel diameter d1 at the point of time at which the dilatation amount R after releasing of the blood vessel from the blood flow obstruction has the maximum value Rmax, and the value of the wall thickness t at the point of time at which the dilatation amount R of the blood vessel 20 has the maximum value Rmax. FIG. 7 is the graph indicating a relationship between the wall thickness t of the blood vessel 20 and the blood vessel diameter d1. It is known that the wall thickness t and the blood vessel diameter d1 are almost proportional to each other, as shown in FIG. 7. In a normal state of the subject person, the blood vessel diameter d1 and the wall thickness t have a proportional relationship as shown in FIG. 7. Where the subject person suffers from hyperpiesia or a renal disease, for example, the wall thickening of the blood vessel 20 takes place, and the blood vessel diameter d1 and the wall thickness t deviate from the above-indicated proportional relationship. Thus, it is considered that an abnormality of the blood vessel function causes a deviation of the wall thickness t and the blood vessel diameter d1 from the normal proportional relationship. It is noted that the male tends to have a larger value of the blood vessel diameter d1 than the female, but the organic index value X2 (wall thickness t/blood vessel diameter d1) does not reflect this sexual difference of the blood vessel diameter d1.

Figure 8:
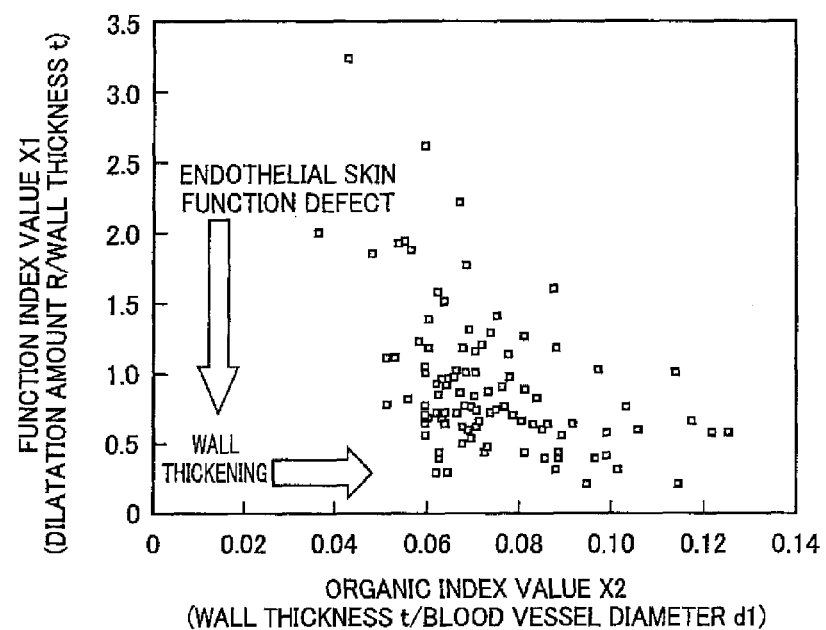
FIG. 8 is a graph indicating a relationship between the function index value (dilatation amount/wall thickness) measured by the blood vessel function inspecting apparatus, and an organic index value (wall thickness/blood vessel diameter)
Figure 9:
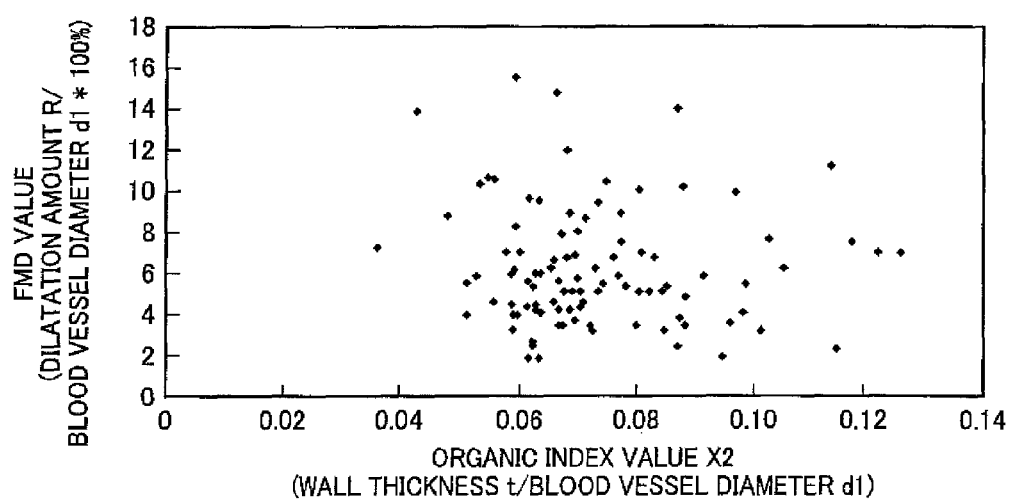
FIG. 9 is a graph indicating a relationship between the FMD value (dilatation amount/rest-time blood vessel diameter*100%), and the organic index value (wall thickness/blood vessel diameter)

The above-described function index value X1 represented as the dilatation amount R/wall thickness t, and the above-described organic index value X2 represented by the wall thickness t/blood vessel diameter d1 are respectively used as a functional change index value and an organic change index value. When these index values X1, X2 are taken along the respective two axes, a graph as shown in FIG. 8 is obtained. This graph indicates that the functional index value X1 (=dilatation amount R/wall thickness t) decreases with an increase of the organic index value X2 (=wall thickness t/blood vessel diameter d1). The functional index value X1 is relatively small where the amount of increase of the wall thickness t is larger than the amount of increase of the blood vessel diameter d1. When the function index value X1 taken along the vertical axis in FIG. 8 is replaced by the known FMD value (=dilatation amount R/rest-time blood vessel diameter da*100%), a graph as shown in FIG. 9 is obtained. In the graph of FIG. 9, the two values have a lower degree of correlation therebetween, than in the graph of FIG. 8. In the graph of FIG. 9, for example, the value (dilatation amount R/blood vessel diameter d1) is relatively large when the value (wall thickness t/blood vessel diameter d1) is relatively large. For this reason, the functional index value X1 (dilatation amount R/wall thickness t) and the organic index value X2 (wall thickness t/blood vessel diameter d1) shown in the graph of FIG. 8 can be used as index values representing the functional and organic changes of the blood vessel 20 and effective to implement the diagnosis of the blood vessel function, because those index values X1, X2 have a relatively high degree of tendency of correlation therebetween as described above.

The blood vessel function index value calculating portion 86 is further configured to calculate a function/organic index value X3 [=index value X1 (dilatation amount R/wall thickness t)/index value X2 (wall thickness t/blood vessel diameter d1)] on the basis of both of the above-described functional change value (dilatation R/wall thickness t) and organic change value (wall thickness t/blood vessel diameter d1), namely, by dividing the functional index value X1 by the organic index value X2. The above-described function/organic index value X3 represents the functional change with respect to the organic change, and a decrease of the value represented by (dilatation amount R/wall thickness t) results in a decrease of the function/organic index value X3. The amount of decrease of the function/organic index value X3 which involves the organic change (wall thickness t/blood vessel diameter d1) is larger than the amount of decrease of the function index value X1. It is noted that the FMD value (dilatation amount R/blood vessel diameter d1*100%) is obtained by changing the denominator of the function/organic index value X3 to its reciprocal (blood vessel diameter d1/wall thickness t). In this case, the FMD value tends to improve as a result of the wall thickening, as is apparent from the graph of FIG. 9, so that the FMD value has a large degree of data variation.

Figure 10:
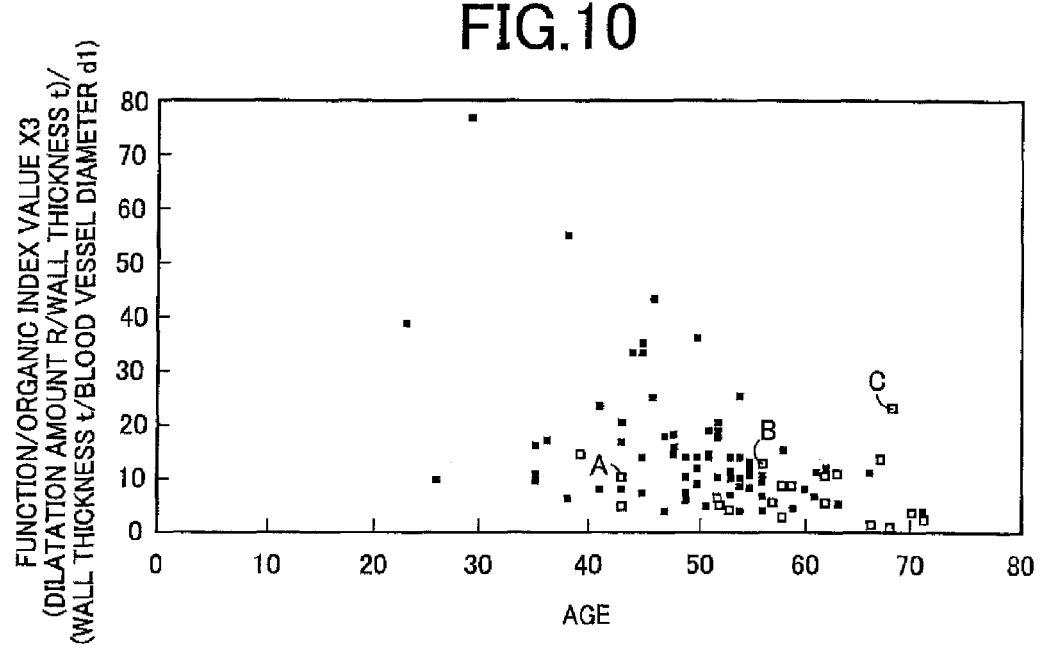
FIG. 10 is a graph indicating a relationship between the function/organic index value measured by the blood vessel function inspecting apparatus, and an age of the subject person.
Figure 11:
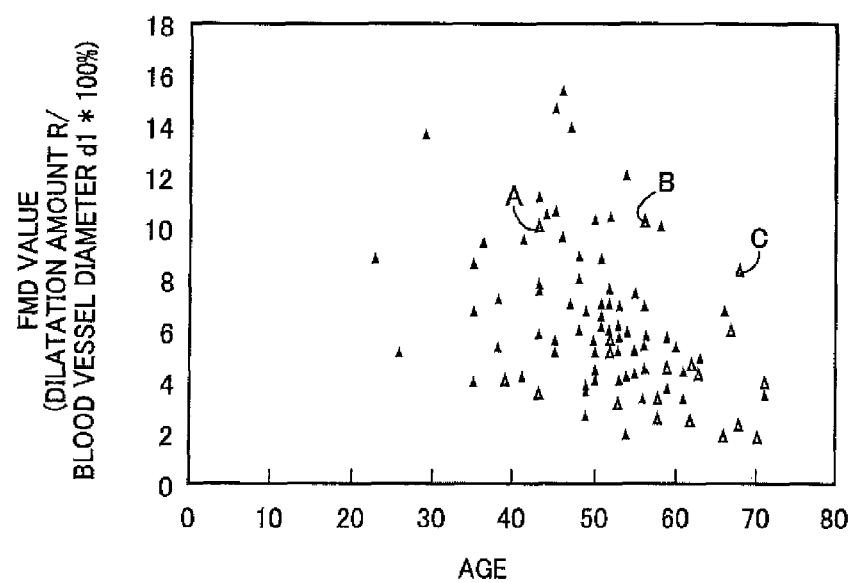
FIG. 11 is a graph indicating a relationship between the FMD value (dilatation amount/rest-time blood vessel diameter*100%), and the age.
Figure 12:
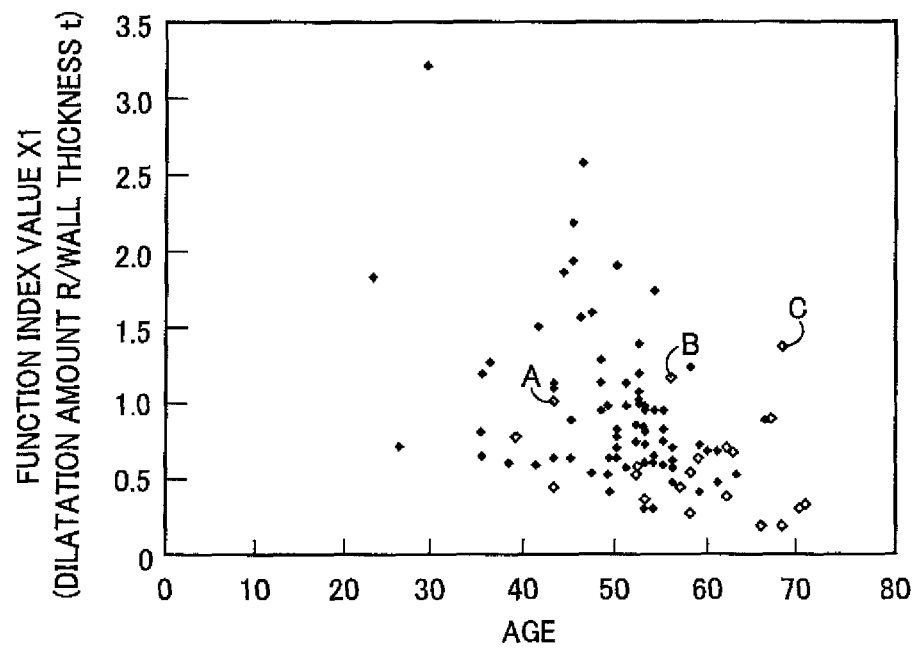
FIG. 12 is a graph indicating a relationship between the function index value (dilatation amount/wall thickness) measured by the blood vessel function inspecting apparatus, and the age.

Graphs of FIGS. 10-12 indicate relationships of the index values and the age of the subject person. FIG. 10 is the graph indicating the relationship between the function/organic index value X3 [=(dilatation amount R/wall thickness t)/ (wall thickness t/blood vessel diameter d1)], and the age of the subject person, and FIG. 11 is the graph indicating the relationship between the FMD value (dilatation amount R/blood vessel diameter d1*100%) and the age, while the FIG. 12 is the graph indicating the relationship between the function index value X1 (dilatation amount R/wall thickness t) and the age. The graphs of the above-indicated figures are obtained from the index values which are calculated on the basis of the same set of measurement data. In the graphs of FIGS. 10-12, black marks indicate values of healthy subject persons, while white marks indicate values of unhealthy subject persons which suffer from at least one of cardiovascular diseases, hyperpiesia, diabetes and dyslipidemia. As is apparent from each of the graphs of FIGS. 10-12, the index values decrease (the blood vessel function decreases) with an increase of the age.

In the graph of FIG. 11 indicating the relationship between the FMD value and the age, most of the subject persons (indicated by the white triangular marks) suffering from any one of the above-indicated diseases have relatively small FMD values, but the FMD values of the subject persons A, B and C deviate from the FMD values of the other unhealthy subject persons. Namely, the FMD values of the unhealthy subject persons A, B and C are more or less similar to those of the healthy subject persons (indicated by the black triangular marks). The graph of FIG. 12 is obtained by replacing the FMD value taken along the vertical axis in the graph of FIG. 11 by the functional index value X1 (dilatation amount R/wall thickness t). In the graph of FIG. 12, the function index values X1 of the unhealthy subject persons A, B and C have smaller differences with respect to those of the other unhealthy subject persons, than in the graph of FIG. 11. In the graph of FIG. 10 indicating the relationship between the function/organic index value X3 and the age, the function/organic index values X3 of the unhealthy subject persons A, B and C have smaller differences with respect to those of the other unhealthy subject persons (indicated by white square marks), than in the graph of FIG. 12. In particular, the differences of the function/organic index values X3 of the unhealthy subject persons A and B with respect to those of the other unhealthy subject persons are considerably reduced, and the values X3 of the subject persons A and B are similar to those of the other subject persons in the unhealthy group. Thus, the measurement data processed with respect to the function index value X1 and the function/organic index value X3 have a smaller degree of variation than the conventional FMD value, and permit easier distinction between the healthy subject persons and the unhealthy subject persons, and easier evaluation of the blood vessel function of the subject persons, than the conventional FMD value.

Referring back to FIG. 5, the blood vessel function diagnosing portion 88 is configured to implement a diagnosis of the blood vessel function on the basis of the relationship of FIG. 8, the relationship of FIG. 10 or the relationship of FIG. 12, for example. According to the relationship of FIG. 8, for example, the value (dilatation amount R/wall thickness t) tends to decrease with an increase of the value (wall thickness t/blood vessel diameter d1). The blood vessel function diagnosing portion 88 implements the diagnosis of the blood vessel function by determining whether the value (dilatation amount R/wall thickness t) falls within a predetermined range of the above-indicated tendency obtained by experimentation, and if the value does not fall within the predetermined range, implements the diagnosis on the basis of the direction of deviation of the value from the predetermined range, and the amount of difference of the value from the predetermined range. Where the diagnosis of the blood vessel function is implemented on the basis of the relationship of FIG. 10, namely, on the basis of the function/organic index value X3, the blood vessel function diagnosing portion 88 determines whether the function/organic index value X3 is smaller than a reference value predetermined by experimentation for each age.

The display control portion 90 is configured to control the monitoring image display device 30 to display a two-dimensional graph indicative of the relationship of FIG. 8 between the function index value X1 and the organic index value X2, and to also display optimum ranges of the values predetermined by experimentation, for easier diagnosis of the blood vessel function. The display control portion 90 is further configured to control the monitoring image display device 30 to display the graph indicative of the relationship obtained in the last measurement and stored in a memory portion 92, together with the relationship obtained in the present measurement, making it possible to recognize a change of the blood vessel function from the last measurement to the present measurement, and permitting a visual checking of the degree of recovery of the blood vessel function, and as to whether the present remedy is correct or not.

Figure 13:
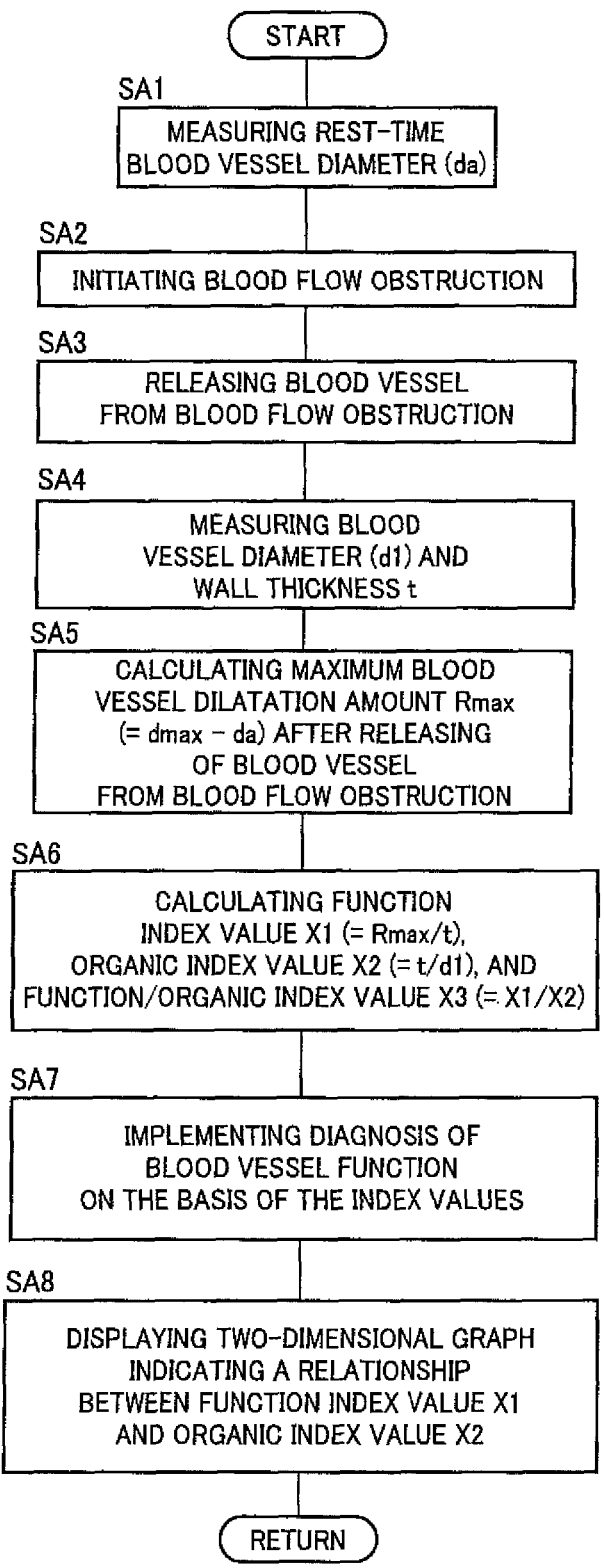
FIG. 13 is a flow chart illustrating major control operations of the blood vessel function inspecting apparatus (electronic control device), namely, control operations to calculate the function index value on the basis of the dilatation amount after releasing of the blood vessel from blood flow obstruction, to calculate the organic index value, and to implement a diagnosis of the blood vessel function on the basis of the above-indicated index values.

FIG. 13 is the flow chart illustrating major control operations of the blood vessel function inspecting apparatus 22 (electronic control device 28), namely, control operations to calculate the function index value X1 on the basis of the dilatation amount R after releasing of the blood vessel from the blood flow obstruction, to calculate the organic index value X2 and the function/organic index value X3, and to implement the diagnosis of the blood vessel function on the basis of the above-indicated index values.

Initially, step SA1 (hereinafter "step" being omitted) corresponding to the blood vessel diameter measuring portion 80 is implemented to measure the blood vessel diameter da before the blood flow obstruction while the subject person is at rest. Then, the control flow goes to SA2 corresponding to the cuff pressure control portion 94, to raise the cuff pressure for obstructing the blood flow through the blood vessel 20 for a predetermined length of time while the subject person is at rest. For instance, the blood flow obstruction of the blood vessel 20 is maintained for about five minutes. After the obstruction of the blood flow through the blood vessel 20 is maintained for the predetermined length of time, SA3 also corresponding to the cuff pressure control portion 94 is implemented to evacuate the cuff 21 for releasing the blood vessel 20 from the blood flow obstruction. SA4 corresponding to the blood vessel diameter measuring portion 80 and the blood vessel wall thickness measuring portion 84 is then implemented to initiate continuous measurements of the blood vessel diameter d1 and the blood vessel wall thickness t upon releasing of the blood vessel 20 from the blood flow obstruction. The measurements are continued for a predetermined length of time (about 60 seconds, for instance). Then, SA5 corresponding to the blood vessel function index value calculating portion 86 is implemented to calculate the maximum value Rmax (=dmax−da) of the dilatation amount of the blood vessel, which is a difference between the maximum value dmax of the blood vessel diameter values d1 measured during the predetermined measurement length of time, and the rest-time blood vessel diameter da. SA6 also corresponding to the blood vessel function index value calculating portion 86 is implemented to calculate the function index value X1 (=maximum value Rmax/wall thickness t) on the basis of the maximum value Rmax of the blood vessel dilatation amount calculated in SA5, to further calculate the organic index value X2 (=wall thickness t/blood vessel diameter d1), and to further calculate the function/organic index value X3 (=X1/X2) on the basis of the calculated function index value X1 and organic index value X2. For example, the wall thickness t used in SA6 is the value t at the point of time at which the maximum value Rmax of the blood vessel dilatation amount R is measured. Then, SA7 corresponding to the blood vessel function diagnosing portion 88 is implemented to implement the diagnosis of the blood vessel function on the basis of the calculated index values (X1-X3) as compared with predetermined respective optimum ranges of the index values. In SA8 corresponding to the display control portion 90, the monitoring image display device 30 displays a two-dimensional graph indicating a relationship between the function index value X1 and the organic index value X2, permitting visual recognition of the blood vessel function.

As described above, the present embodiment is configured to calculate the function index value X1 (dilatation amount R/wall thickness t) for diagnosing the blood vessel of its function, after releasing of the blood vessel from the blood flow obstruction, by dividing the dilatation amount R of the blood vessel diameter d1 continuously measured by the blood vessel diameter measuring portion 80, by the wall thickness t measured by the blood vessel wall thickness measuring portion 84, so that the blood vessel can be diagnosed of its function with a higher degree of accuracy than in the prior art. For instance, the prior art uses an index value (FMD value: dilatation amount R/blood vessel diameter d1*100%) obtained by dividing the dilatation amount R of the blood vessel after releasing of the blood vessel from the blood flow obstruction, by the blood vessel diameter d1, for diagnosing the blood vessel of its function on the basis of the thus obtained index value. Since the amount of change of the function index value according to the invention with a change of the function of the blood vessel is larger than that of the prior art index value (FMD value), the diagnosis of the blood vessel function can be implemented more adequately on the basis of the function index value. Namely, the function index value X1 more accurately reflects a change of the blood vessel function than the prior art index value, since the amount of change of the wall thickness t is larger than the amount of change of the blood vessel diameter d1.

The present embodiment is further configured such that the blood vessel function index value calculating portion 86 calculates the organic index value X2, by dividing the wall thickness t by the blood vessel diameter d1, so that the blood vessel is diagnosed of its function on the basis of the relationship between the function index value X1 and the organic index value X2. The function index value X1 tends to decrease with an increase of the organic index value X2, so that the diagnosis of the blood vessel function can be implemented more accurately on the basis of the above-indicated tendency. For instance, the blood vessel function can be diagnosed for any abnormality, on the basis of a direction and a degree of deviation of the measurement data from the above-indicated tendency.

The present embodiment is further configured such that the blood vessel function index value calculating portion 86 calculates the function/organic index value X3, by dividing the function index value X1 by the organic index value X2, so that the blood vessel is diagnosed of its function on the basis of the function/organic index value X3. The measurement data processed with respect to the function/organic index value X3 has a reduced degree of variation, permitting an improved accuracy of diagnosis of the blood vessel function.

Then, a blood vessel function inspecting apparatus 95 according to another embodiment of this invention will be described. In the following description, the same reference signs as used in the preceding embodiment will be used to identify the corresponding elements, which will not be described redundantly.

Embodiment 2

The above-described electronic control device 28 shown in FIG. 1, which has the functions described above, has also a function of measuring a blood flow velocity distribution DS in a non-invasion manner, by irradiating the ultrasonic waves from the long-axis ultrasonic detector array C toward the blood vessel 20 within the live body 14 through the skin. Then, the electronic control device 28 calculates a blood viscosity distribution DV and a blood shear rate distribution DSR within the blood vessel 20, on the basis of the measured blood flow velocity distribution DS, and further calculates a blood shear stress distribution DSS on the basis of the blood viscosity distribution DV and the blood shear rate distribution DSR.

The electronic control device 28 is further configured to measure the blood pressure by the oscillometric method using the cuff 21 wound on the brachium. Namely, the pressure within the cuff 21 detected by a pressure sensor 23 is raised with a pump 25 and the pressure control valve 29, to a blood flow obstruction value higher than the systolic blood pressure (highest blood pressure) of the subject person, and is then gradually lowered at a predetermined rate. During a period of the gradual lowering of the pressure of the cuff 21, a pressure pulsation wave generated in synchronization with the heart beat pulses, that is, a pulse wave is extracted to find points of inflection of an envelope connecting the amplitude values of the pulse wave, that is, a maximum value of a difference of the amplitude values, and to determine the pressure values of the cuff 21 corresponding to the maximum value, as a systolic blood pressure value SBP and a diastolic blood pressure value DBP. Further, the pressure value of the cuff 21 corresponding to the maximum value of the pulse wave amplitude values is determined as a mean blood pressure value MBP.

Figure 14:
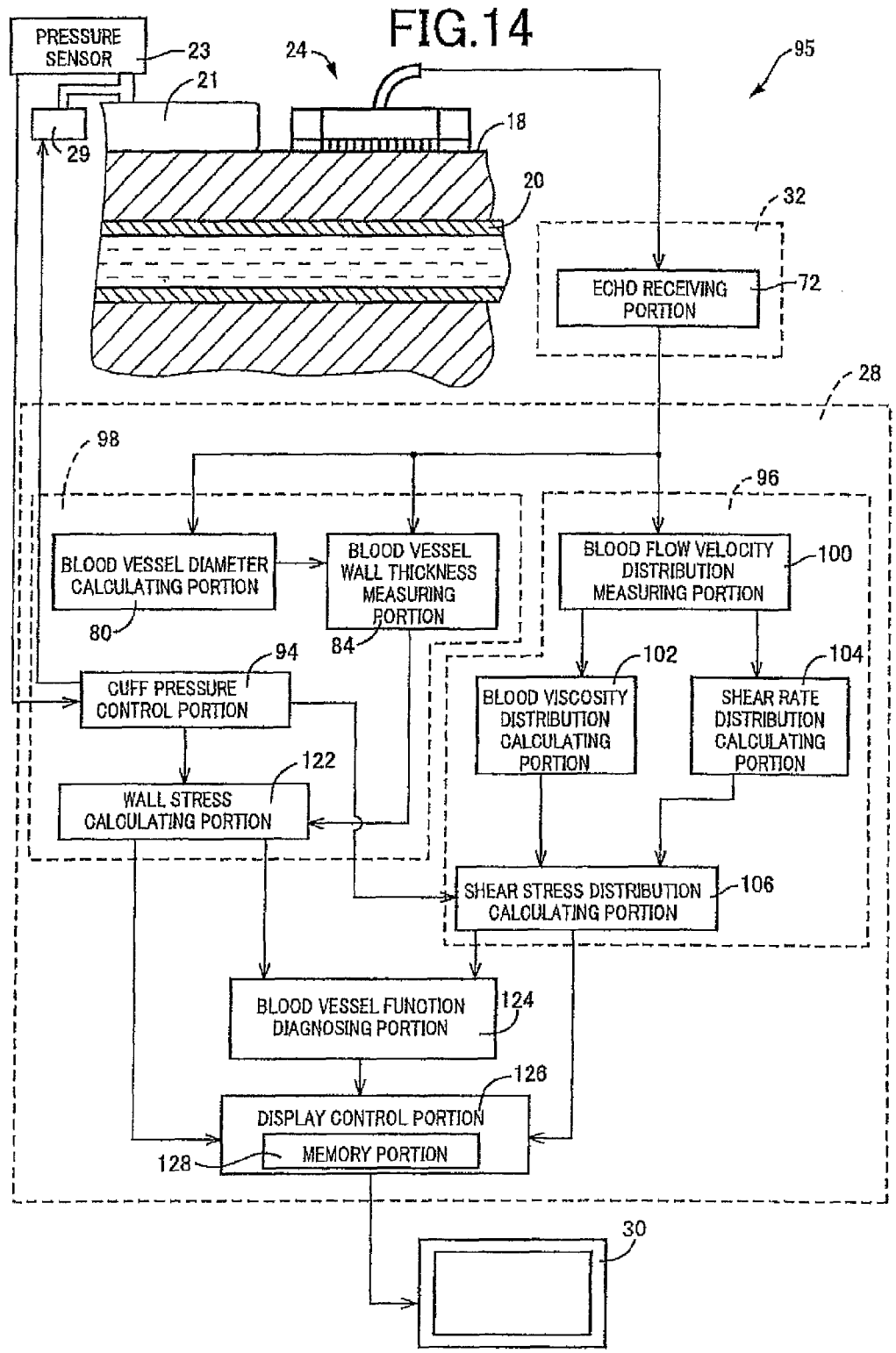
FIG. 14 is a functional block diagram for explaining major control functions of a blood vessel function inspecting apparatus according to another embodiment of this invention.

FIG. 14 is the functional block diagram for explaining major control functions of the blood vessel function inspecting apparatus 95 according to the present embodiment of this invention. Since the mechanical elements in this embodiment are identical with those in the preceding embodiment, the mechanical elements will not be described. The blood vessel diameter measuring portion 80 and the blood vessel wall thickness measuring portion 84 in the present embodiment are basically identical with those in the preceding embodiments, these portions 80, 84 will not be described, either.

The echo receiving portion 72 is configured to receive the reflected waves of the ultrasonic beams generated from the ultrasonic probe 24, and supply the reflected waves to the electronic control device 28. For example, the echo receiving portion 72 receives the reflected waves of the ultrasonic beam generated from the first short-axis ultrasonic detector array A, and supplies the reflected waves to the blood vessel diameter measuring portion 80 and the blood vessel wall thickness measuring portion 84. Further, the echo receiving portion 72 receives the reflected waves of the ultrasonic beam generated from the long-axis ultrasonic detector array C, and supplies the reflected waves to a blood flow velocity distribution measuring portion 100.

Figure 15:
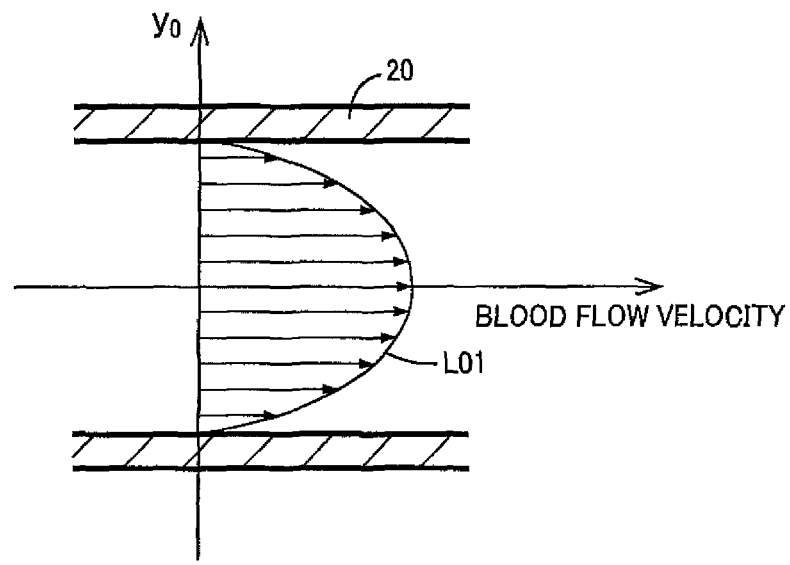
FIG. 15 is an illustrative view indicating a blood flow velocity distribution to be measured by a blood flow velocity distribution measuring portion of the blood vessel function inspecting apparatus of FIG. 14.
Figure 16:
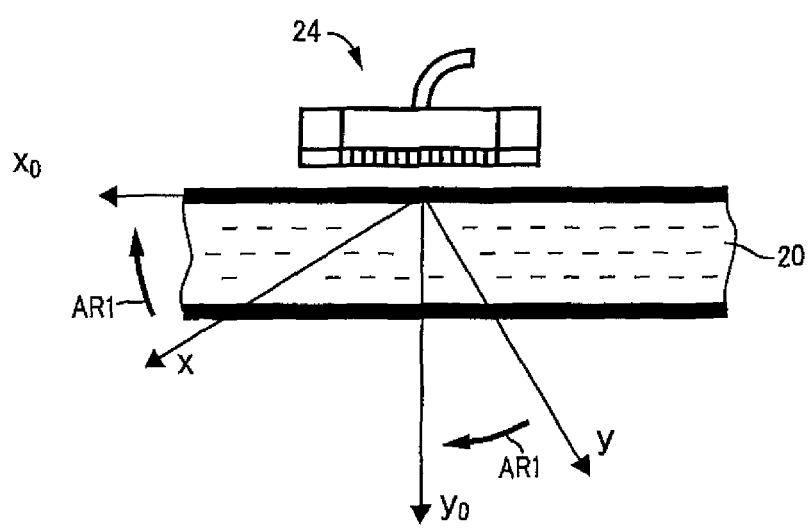
FIG. 16 is a view for explaining reference characters in an equation used for calculating the blood flow velocity distribution to be measured by a blood flow velocity distribution measuring portion of the blood vessel function inspecting apparatus of FIG. 14.

The blood flow velocity distribution measuring portion 100 is configured to determine the position of the blood vessel 20 by a tomographic image generated on the basis of scattered ultrasonic waves (reflected waves) received by the long-axis ultrasonic detector array C of the ultrasonic probe 24, and at the same time obtain a two-dimensional velocity vector distribution in a two-dimensional tomographic plane. Although the velocity vector distribution to be obtained may be either two-dimensional or three-dimensional, the two-dimensional velocity vector distribution is obtained in the present embodiment, for simplifying the processing operation, and the two-dimensional velocity vector distribution is referred to as a blood flow velocity distribution DS in blood flow velocity distribution measuring portion 100. A solid line L01 in the illustrative view of FIG. 15 represents an instantaneous blood flow velocity distribution DS. The above-described two-dimensional velocity vector distribution or three-dimensional velocity vector distribution can be obtained by obtaining a distance of movement of blood cells by a phase correlation method using two ultrasonic tomographic images or three-dimensional volume images (each being chronologically continuous) obtained at a predetermined time interval, and by dividing the obtained distance of movement by the time interval of the two images. Alternatively, the blood flow velocity distribution measuring portion 100 can obtain a perfect two-dimensional velocity vector distribution by obtaining a velocity component in the direction of irradiation of the ultrasonic wave (which is one of velocity components of the two-dimensional velocity vector) by a method similar to a well known color Doppler method, then obtaining the other velocity component normal to the obtained one velocity component, using a incompressibility condition in the fluid dynamics as represented by the following Equation (1) stored in a memory. As described above, the blood flow velocity distribution measuring portion 100 measures the blood flow velocity distribution DS within the blood vessel 20 in the non-invasion manner with the ultrasonic waves irradiated toward the blood vessel 20 in the live body 14 through the skin. Needless to confirm, before the blood flow velocity distribution measuring portion 100 implements the measurement of the blood flow velocity distribution DS, the ultrasonic probe 24 is positioned in the above-described predetermined measuring position with respect to the blood vessel 20. As indicated in FIG. 16, "x", "y", "u" and "v" in the following Equation (1) respectively represent: a position in a direction perpendicular to the ultrasonic wave beam axis; a position in the direction of the ultrasonic wave beam axis (in the direction of irradiation of the ultrasonic wave); a velocity component in the x direction; and a velocity component in the direction of the ultrasonic wave beam axis, that is, in the y direction.

[Equation 1]

$$\frac{\partial u}{\partial x} + \frac{\partial v}{\partial y} = 0 \qquad (1)$$

The blood flow velocity distribution measuring means 100 can measure the blood flow velocity distribution DS instantaneously at a predetermined point of time, and continuously for a predetermined length of time.

Figure 17:
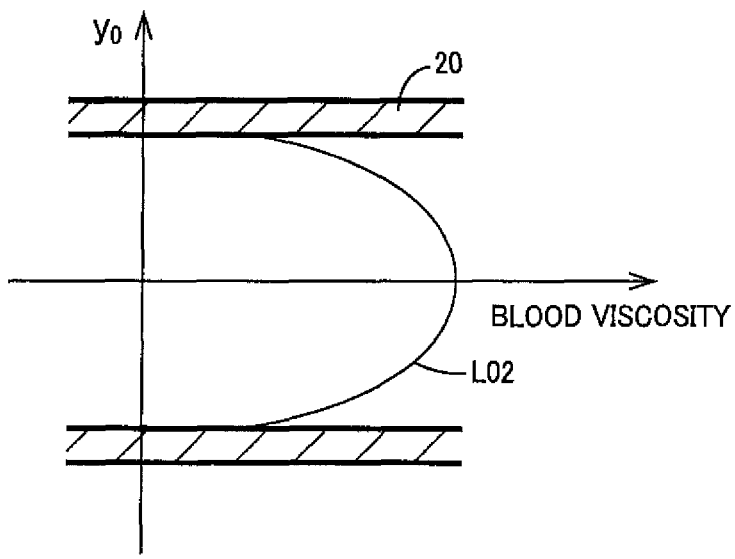
FIG. 17 is an illustrative view indicating a blood viscosity distribution calculated by a blood flow viscosity distribution measuring portion of the blood vessel function inspecting apparatus of FIG. 14.

A blood viscosity distribution calculating portion 102 is configured to calculate the viscosity distribution DV of the blood (blood viscosity distribution DV) within the blood vessel 20 under measurement, on the basis of the blood flow velocity distribution DS measured by the blood flow velocity distribution measuring portion 100, and according to two-dimensional Navier-Stokes equations which are stored in the memory and which are represented by the following Equations (2) and (3). A solid line L02 in the illustrative view of FIG. 17 indicates an example of the instantaneous blood viscosity distribution DV, which has non-Newton characteristics of the blood. The blood viscosity distribution calculating portion 102 is further configured to calculate a mean value of the blood viscosity μ on the basis of the blood viscosity distribution DV, for quantitative determination of the blood viscosity μ. Where the blood flow velocity distribution DS is a three-dimensional velocity vector distribution, the blood viscosity distribution DV is calculated according to the Navier-Stokes equations which are three-dimensional.

[Equation 2]

$$\frac{\partial u}{\partial t} + u\frac{\partial u}{\partial x} + v\frac{\partial u}{\partial y} = -\frac{1}{\rho}\frac{\partial p}{\partial x} + v\left(\frac{\partial^2 u}{\partial x^2} + \frac{\partial^2 u}{\partial y^2}\right) \qquad (2)$$

[Equation 3]

$$\frac{\partial v}{\partial t} + u\frac{\partial v}{\partial x} + v\frac{\partial v}{\partial y} = -\frac{1}{\rho}\frac{\partial p}{\partial y} + v\left(\frac{\partial^2 v}{\partial x^2} + \frac{\partial^2 v}{\partial y^2}\right) \qquad (3)$$

[Equation 4]

$$v = \frac{\mu}{\rho} \qquad (4)$$

[Equation 5]

$$v = \frac{\frac{\partial \xi}{\partial t} + u\frac{\partial \xi}{\partial v} + v\frac{\partial \xi}{\partial y}}{\frac{\partial^2 \xi}{\partial x^2} + \frac{\partial^2 \xi}{\partial y^2}} \qquad (5)$$

[Equation 6]

$$\xi = \frac{\partial u}{\partial y} - \frac{\partial v}{\partial x} \qquad (6)$$

In the above Equations (2) and (3), the reference characters "x", "y", "u" and "v" are the same as those in the above Equation (1), and "t", "p", "ρ" and "v" respectively represent: time; pressure; density of the blood; and kinematic viscosity (coefficient of kinematic viscosity). Where the blood has the viscosity (coefficient of viscosity) μ, the kinematic viscosity ν is calculated according to the above Equation (4). Alternatively, the kinematic viscosity ν can be obtained according to the above Equation (5) which is derived by deleting the term of the pressure "p" included in the above Equations (2) and (3), by differentiation. In the Equation (5), "ξ" represents the vorticity, which is calculated according to the above Equation (6) and is defined by the velocity vector component only, as is apparent from this Equation (6).

Figure 18:
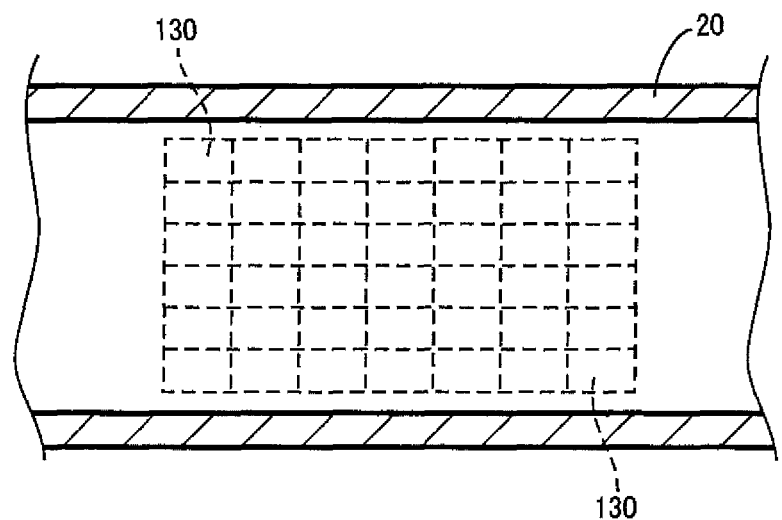
FIG. 18 is a view indicating an example of virtual division of a space within the blood vessel the blood flow velocity distribution of which is measured with the ultrasonic wave generated from the ultrasonic probe of FIG. 2, wherein the space is divided into a plurality of smaller sub-regions.

When the blood viscosity distribution calculating portion 102 calculates the blood viscosity distribution DV on the basis of the blood flow velocity distribution DS, the blood is presumed to be incompressible, and the space within the blood vessel 20 is virtually divided into a plurality of smaller sub-regions 130, as shown in FIG. 18. The blood viscosity distribution calculating portion 102 applies the above-described Navier-Stokes equations to each of the sub-regions 130 on the assumption that the density p and viscosity μ of the blood is constant in each sub-regions 130, and combines together the values of the blood viscosity μ calculated for the respective sub-regions 130, to calculate the blood viscosity distribution DV.

A shear rate distribution calculating portion 104 is configured to calculate the shear rate distribution DSR of the blood (blood shear rate distribution DSR) within the blood vessel 20 under measurement, on the basis of the blood flow velocity distribution DS measured by the blood flow velocity distribution measuring portion 100. Described more specifically, the shear rate distribution calculating portion 104 obtains a two-dimensional shear rate tensor on the basis of the blood flow velocity distribution DS (two-dimensional velocity vector distribution), and determines, by approximation, the normal direction of the blood vessel 20 to be a direction normal to a line of the blood flow a direction of tangency of which is parallel to the direction of the above-described two-dimensional velocity vector. The shear rate distribution calculating portion 104 obtains a shear component $e_{xy0}$ by rotatory coordinate conversion (indicated by arrow-headed lines AR1 in FIG. 16) of the above-described two-dimensional shear rate component with respect to the normal direction of the blood vessel 20 determined by approximation as described above, and extracts the shear component $e_{xy0}$ as the blood shear rate SR, to calculate the blood shear rate distribution DSR. A solid line L03 in the illustrative view of FIG. 19 indicates an example of the instantaneous blood shear rate distribution DSR. The shear rate distribution calculating portion 104 is further configured to calculate an mean value of the blood shear rate SR on the basis of the blood shear rate distribution DSR, for quantitative determination of the shear rate SR of the blood (blood shear rate SR). It is noted that the above-described shear component $e_{xy0}$ is represented by the following Equation (7), which is stored in the blood shear rate distribution calculating portion 104. Where the above-described blood flow velocity distribution DS is a three-dimensional velocity vector distribution, the blood shear rate distribution DSR is calculated according to the above-described shear rate tensor which is three-dimensional. The values $x_0$, $y_0$, $u_0$ and $v_0$ in the following Equation (7) are obtained by rotatory coordinate conversion (indicated by the arrow-headed lines AR1 in FIG. 16) of the values x, y, u and v in the above Equation (1), and the $y_0$ axis coincides with the direction normal to the blood vessel wall, and the $x_0$ axis coincides with the longitudinal direction of the blood vessel 20, as indicated in FIGS. 2 and 16. Further, the y axis coincides with the direction of the ultrasonic wave beam axis, and the x axis coincides with the direction perpendicular to the ultrasonic wave beam axis. The character "$u_0$" represents the velocity component in the $x_0$ direction, and the reference character "$v_0$" represents the velocity component in the $y_0$ direction.

[Equation 7]

$$e_{xy0} = \frac{1}{2}\left(\frac{\partial u_0}{\partial y_0} + \frac{\partial v_0}{\partial x_0}\right) \qquad (7)$$

When the shear rate distribution calculating portion 104 calculates the blood shear rate distribution DSR on the basis of the blood flow velocity distribution DS, the space within the blood vessel 20 is virtually divided into the plurality of smaller sub-regions 130, as shown in FIG. 18, as in the calculation of the blood viscosity distribution DV, and the shear rate distribution calculating portion 104 applies the above-indicated Equation (7) to each of the sub-regions 130 to calculate the shear component $e_{xy}$ as the blood shear rate SR for each sub-region 130. The shear rate distribution calculating portion 104 calculates the blood shear rate distribution DSR by combining the values of the blood shear rate SR ($e_{xy}$) calculated for the respective sub-regions 130.

A shear stress distribution calculating portion 106 stores the Newton's law of viscosity represented by the Equation (8) indicated below, and is configured to calculate a shear stress distribution of the blood (blood shear stress distribution) DSS on the basis of the above-described blood viscosity distribution DV and the blood shear rate distribution DSR and according to the Newton's law of viscosity. The above-described mean value of the blood viscosity μ may be used in place of the above-described blood viscosity distribution DV, to calculate the blood shear stress distribution DSS. A solid line L04 in the illustrative view of FIG. 20 indicates an example of the instantaneous blood shear stress distribution DSS. The shear stress distribution calculating portion 106 calculates a mean value SS of the blood shear stress (hereinafter referred to as "shear stress SS") at each point of time of measurement, on the basis of the blood shear stress distribution DSS, for quantitative determination of the shear stress distribution DSS of the blood (blood shear stress).

The shear stress distribution calculating portion 106 is further configured to calculate a representative value SS1 of the shear stress SS for implementing the diagnosis of the blood vessel function, on the basis of the shear stress SS at each point of measurement. The representative value SS1 (shear stress SS1) of the shear stress SS is calculated at a reference point of time which is just prior to the present point of time by a predetermined length of time corresponding to a delay of a response of a change of a wall stress WS (described below) which takes place with a change of the shear stress SS. Namely, the shear stress SS1 is calculated at the reference point of time which is prior to the present point of time of calculation of the wall stress by a predetermined time of delay of the response. This time of delay of the response is provided in view of a fact that the rate of the blood flow considerably increases immediately after releasing of the blood vessel from the blood flow obstruction upon the FMD evaluation and gradually decreases, and that the endothelial skin of the blood vessel instantaneously responds to the change of the blood flow rate, with a result of production of nitrogen monoxide NO, which diffuses into the inner layer of the blood vessel into the smooth muscles so that the smooth muscles are relaxed. It is confirmed that a delay time exists between the moment of releasing of the blood vessel from the blood flow obstruction and the moment of relaxation of the smooth muscles, so that the above-indicated time of delay of the response is provided. That is, the shear stress SS1 calculated at the reference point of time has a correlation with the wall stress WS calculated at a point of time which is subsequent to the reference point of time by the predetermined time of delay of the response. The use of these shear stress SS1 and wall stress WS as the representative values assures accurate diagnosis of the blood vessel function. The above-indicated time of delay of the response is determined by experimentation, to be about 20-30 seconds, or to be a length of time corresponding to 20-30 heart beat pulses, for example.

The representative value of the shear stress SS1 calculated at the above-indicated reference point of time is one of an integral value of the shear stress values SS at respective points of measurement within a predetermined period of time preceding the reference point of time, a mean value of the shear stress per one heart beat pulse within that predetermined period of time, and an integral or mean value of instantaneous values of the shear stress measured in synchronization with the respective pulses within the predetermined period of time. Namely, the representative value of the shear stress SS1 is calculated on the basis of the shear stress values SS calculated at the respective points of measurement within the predetermined period of time just prior to the above-indicated reference point of time. For instance, the above-indicated predetermined period of time is determined to be a period corresponding to about 20 heart beat pulses generated prior to the above-indicated reference point of time, that is, a period of about 20 heart beat pulses which terminates at the end of the reference point of time. Thus, the representative value of the shear stress SS1 is not an instantaneous value at a given point of time (more specifically, at the predetermined reference point of time), but is calculated on the basis of the shear stress values SS calculated from time to time within the predetermined period of time, so that the representative value of the shear stress SS which reflects stimuli regularly acting on the blood vessel wall are used to implement an adequate diagnosis of the blood vessel function.

[Equation 8]

$$(\text{SHEAR STRESS}) = (\text{VISCOSITY}) \times (\text{SHEAR RATE}) \quad (8)$$

Figure 19:
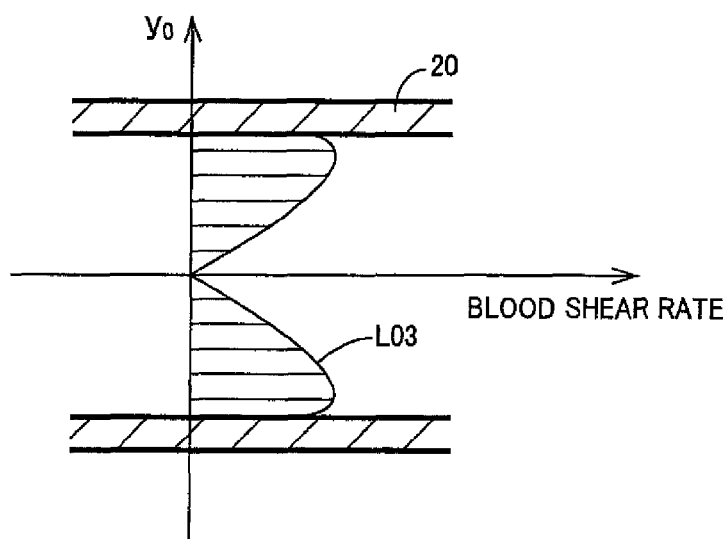
FIG. 19 is an illustrative view indicating a blood shear rate distribution calculated by a shear velocity distribution calculating portion of the blood vessel function inspecting apparatus of FIG. 14.
Figure 20:
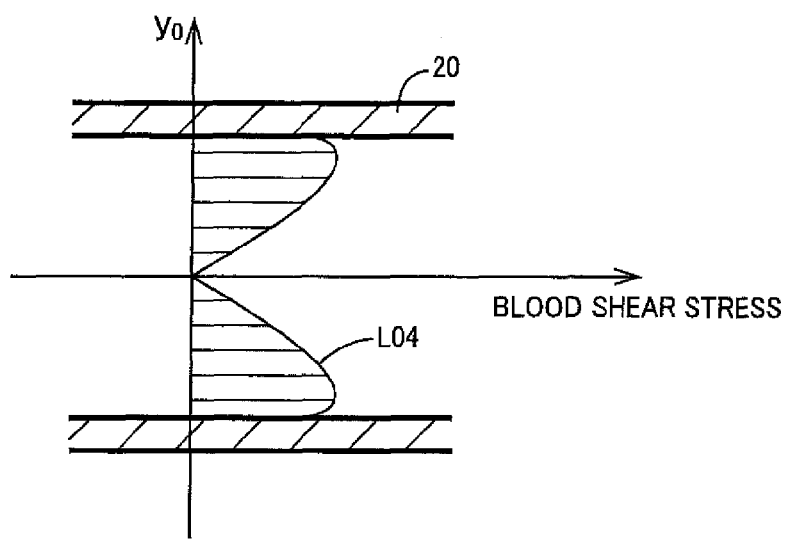
FIG. 20 is an illustrative view indicating a blood shear stress distribution calculated by a shear stress distribution calculating portion of the blood vessel function inspecting apparatus of FIG. 14

When the shear stress distribution calculating portion 106 calculates the blood shear stress distribution DSS on the basis of the above-described blood viscosity distribution DV and blood shear rate distribution DSR, the space within the blood vessel 20 is virtually divided into the plurality of a smaller sub-regions 130 as shown in FIG. 18, as in the case of calculation of the blood viscosity distribution DV and the blood shear rate distribution DSR. The shear stress distribution calculating portion 106 multiplies the blood viscosity µ and the blood shear rate obtained in each of the sub-regions 130, to calculate the blood shear stress in each sub-region 130, according to the above-indicated Newton's law of viscosity, and combines together the values of the blood shear stress calculated for the respective sub-regions 130, to calculate the blood shear stress distribution DSS. It is noted that FIGS. 15, 17, 19 and 20 are illustrative views, and do not necessarily represent the actual distributions, and that the graphs in the coordinate system of FIGS. 19 and 20 are based on the absolute values of the blood shear rate distribution DSR which is deduced from the blood flow velocity distribution DS. It will be understood that the above-described blood flow velocity distribution measuring portion 100, blood viscosity distribution calculating portion 102, shear rate distribution calculating portion 104 and shear stress distribution calculating portion 106 cooperate to constitute a shear stress calculating portion 96, as indicated in FIG. 14.

The blood pressure measuring portion 94 is configured to measure the blood pressure by the oscillometric method, by controlling the air pressure of the cuff 21 wound on the brachium. The blood pressure measuring portion 94 measures the systolic blood pressure SBP and the diastolic blood pressure DBP of the subject person by the oscillometric method well known in the art, on the basis of a change of the amplitude of the pulse wave obtained as pressure pulsation of the cuff 21 in the process of a gradual change of the pressure of the cuff 21. According to the above-indicated oscillometric method, the pressure pulsation wave generated in synchronization with the heart beats in the process of a drop of the pressure of the cuff 21, that is, the pulse wave is extracted to find points of inflection of an envelope connecting the amplitude values of the pulse wave, that is, a maximum value of a difference of the amplitude values, and to determine the pressure values of the cuff 21 corresponding to the maximum value of the difference, as the systolic blood pressure value SBP and the diastolic blood pressure value DBP, and to determine the pressure value of the cuff 21 corresponding to the maximum value of the pressure of the cuff 21, as the mean blood pressure value MBP.

A wall stress calculating portion 122 stores the following Equation (9) as a predetermined equation of a wall stress, and calculates the wall stress WS acting on the wall of the blood vessel 20, on the basis of the blood vessel diameter (endothelial skin diameter) d1 measured by the blood vessel diameter measuring portion 80, the wall thickness t of the blood vessel 20 calculated by the blood vessel wall thickness measuring portion 84, and the blood pressure measured by the blood pressure measuring portion 94 with using the equation of the wall stress. In the present embodiment, the wall stress WS is calculated on the basis of the blood vessel diameter d1 and wall thickness t measured at the point of time of measurement of the diastolic blood pressure DBP used as the representative value, namely, measured at the end of the diastolic period. It is noted that the blood vessel diameter d1 is minimized at the end of the above-indicated diastolic period, so that the end of the diastolic period can be determined by finding the minimum value of the blood vessel diameter d1 which is continuously measured by the above-described blood vessel diameter measuring portion 80 for a predetermined period of time. It will be understood that the above-described blood vessel diameter measuring portion 80, blood vessel wall thickness measuring portion 84, blood pressure measuring portion 94 and wall stress calculating portion 122 cooperate to constitute a wall stress calculating portion as indicated in FIG. 14.

[Equation 9]

$$WS = \frac{DBP \times d_1}{2t} \quad (9)$$

A blood vessel function diagnosing portion 124 is configured to determine whether at least one of the wall stress WS calculated by the wall stress calculating portion 98 and the representative value of the shear stress SS1 (the shear stress SS1) calculated by the shear stress calculating portion 96 is outside a corresponding one of predetermined respective optimum ranges. The shear stress and wall stress are index values effective for implementing a diagnosis of the blood vessel function, and have a close relationship with each other. For instance, the shear stress SS1 varies with a change of the rate of the blood flow through the blood vessel 20, and a change of hematocrit or protein in the blood. As the shear stress SS1 increases, the amount of nitrogen monoxide NO produced from the vascular cells increases, and the blood vessel 20 dilates so as to reduce the shear stress SS1, thus functioning to compensate for an increase of the shear stress SS1. As the blood vessel 20 is dilated, on the other hand, the wall stress WS increases, as is understood from the Equation (9). In this case, the wall thickness t of the blood vessel 20 increases so as to reduce the wall stress WS. Although the values of the shear stress SS and the wall stress WS fall within the optimum ranges when the shear stress SS and wall stress WS have come into a state of equilibrium, the wall stress may transiently increase and deviate from the optimum range. When the nitrogen monoxide NO is inactivated due to oxidization stress, for example, the dilatation of the blood vessel 20 is restricted so that the shear stress SS1 remains at a high level. In this case, peripheral blood vessels have a high degree of resistance, causing a rise of the blood pressure and consequent dilatation of the blood vessel 20. In this state, too, the wall stress SS1 increases, and the wall thickness t increases as an adaptive response (to perform a compensating function). In this transient state, both of the shear stress SS1 and the wall stress WS remain at high levels. In this connection, it is noted that the above-described transient change takes place very slowly, and the equilibrium is established with a time lapse of from about several weeks to about several months. Accordingly, it is necessary to implement successive calculation of the changes of the shear stress SS1 and wall stress WS, for monitoring state of deviation, such as the amount of deviation of the shear and wall stresses SS1 and WS from the respective optimum ranges, and state of recovery, such as the number of hours (number of days) for recovery from the deviation, on the basis of results of the calculation, and comparing the monitored amount of deviation and number of hours with threshold values. Thus, the blood vessel function is evaluated, for early discovery of arteriosclerosis, for example.

The blood vessel function diagnosing portion 124 determines whether the calculated wall stress WS is held within the predetermined optimum range defined by an upper limit WShi and a lower limit WSlo. Further, the blood vessel function diagnosing portion 124 determines whether the calculated shear stress SS1 is held within the predetermined optimum range defined by an upper limit SShi and a lower limit SSlo. The blood vessel function diagnosing portion 124 determines that the blood vessel function is normal, if the wall stress WS is held within the optimum range while at the same time the shear stress SS1 is held within the optimum range. If at least one of the wall stress WS and the shear stress SS1 is outside the corresponding optimum range, the blood vessel function diagnosing portion 124 determines that the blood vessel function is abnormal.

It is difficult to recognize a cause for an abnormality of the blood vessel function, and an adequate remedy for curing the abnormality, where the abnormality is found as a result of the determination on the basis of a single measurement that at least one of the shear stress SS1 and the wall stress WS deviates from the optimum range. However, the calculation of the changes of the shear stress SS1 and wall stress WS for comparison of the calculated amounts of their deviation from the threshold values from time to time makes it possible to find the cause and adequate remedy for the abnormality, and to check an effect of the remedy. For instance, where the shear stress SS1 deviates from the optimum range, the cause and remedy (and the effect of the remedy) for the abnormality can be found synthetically on the basis of the state and speed of recovery into the optimum range, and the state of change of the wall stress WS with the change of the shear stress SS1.

The optimum ranges of the wall stress WS and the shear stress SS1 are determined by experimentation. For instance, the wall stress WS and shear stress SS1 of a plurality of healthy subject persons are measured a plurality of times, to determine average values of the wall stress WS and shear stress SS1 as a reference wall stress WSave and a reference shear stress SSave. The optimum ranges are defined by the respective upper limits (WShi, SShi) which are +10% values of the reference wall stress WSave and shear stress SSave, and the respective lower limits (WSlo, SSlo) which are −10% values of the reference wall stress WSave and shear stress SSave.

Figure 21:
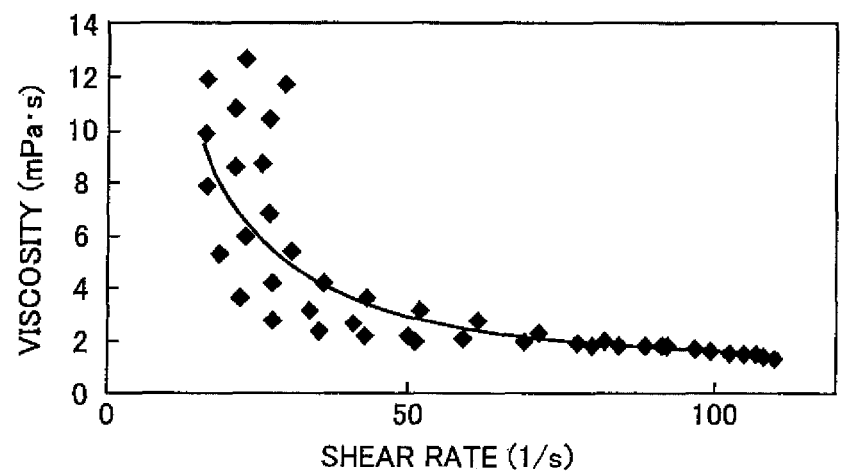
FIG. 21 is a graph indicating a relationship between the shear rate and viscosity measured of healthy subject persons.

FIG. 21 is the graph indicating a relationship between the shear rate SR and the viscosity μ measured of the healthy subject persons. A solid line in the figure is a hyperbola approximated on the basis of a plurality of points of measurement. The shear stress is calculated by multiplying the shear rate SR and the viscosity μ. The shear stress is constant at any point on the hyperbola, and the shear stress value represented by this hyperbola is equivalent to the above-indicated reference shear stress SSave.

Figure 22:
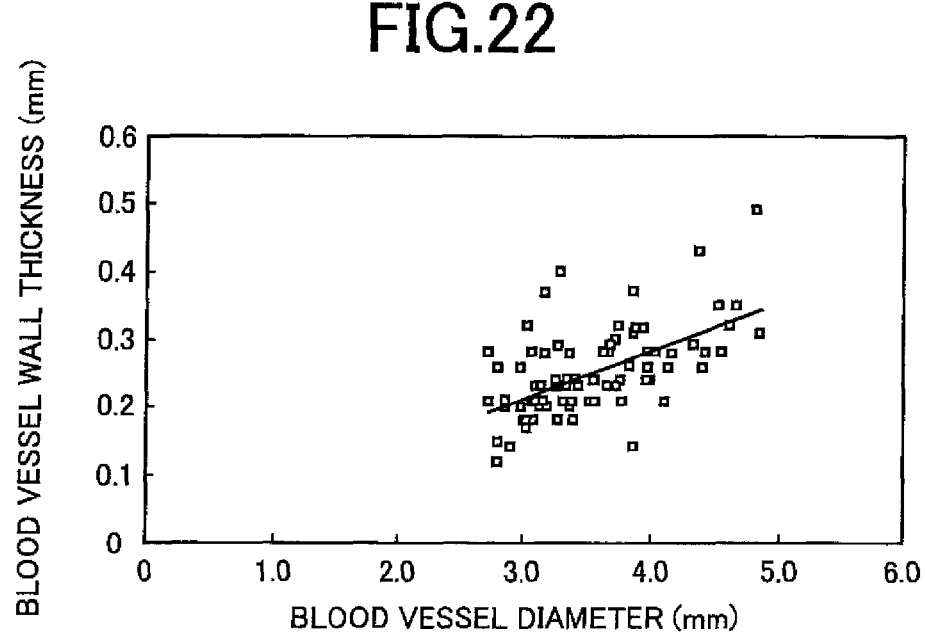
FIG. 22 is a graph indicating a relationship between the diameter and wall thickness of the blood vessel measured of the healthy subject persons.

FIG. 22 is the graph indicating a relationship between the diameter d1 and the wall thickness t of the blood vessel 20 measured of the healthy subject persons. A solid line in the figure is a line approximated according to a linear function on the basis of a plurality of points of measurement. The reference wall stress SSave is determined on the basis of the above-indicated approximated line, or the corresponding blood pressure (diastolic blood pressure DBP, for example).

The optimum ranges may be determined in other manners. For instance, the wall stress WS and shear stress SS1 of a plurality of subject persons are measured, and the optimum ranges are synthetically determined on the basis of results of the measurement while taking account of the states of health of the subject persons. Different optimum ranges are provided for respective different age groups and/or the respective different sexes, for instance.

Figure 23:
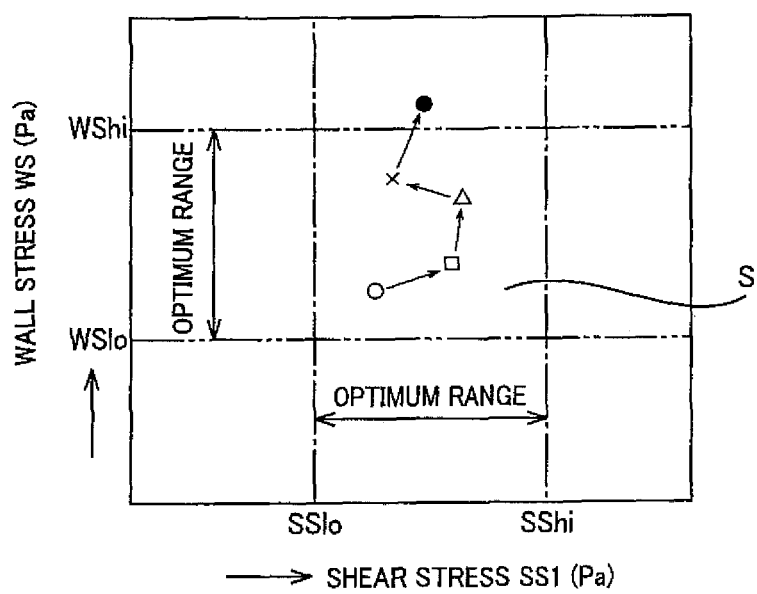
FIG. 23 is a view showing an example of a two-dimensional graph which is displayed on a monitoring image display device of FIG. 14 and which indicates a relationship between a shear stress and a wall stress.

The display control portion 126 is configured to control the monitoring image display device 30 to display numerically or graphically the calculated shear stress SS1 and wall stress WS, in a two-dimensional graph. For example, the monitoring image display device 30 displays the results of measurement in a two-dimensional coordinate system in which the shear stress SS1 (representative value) is taken along the horizontal axis while the wall stress WS is taken along the vertical axis, as indicated in FIG. 23, by way of example. In the example of the two-dimensional graph of FIG. 23, one-dot chain lines indicate the upper limit SShi and lower limit SSlo of the optimum range of the shear stress, while two-dot chain lines indicate the upper limit WShi and lower limit WSlo of the optimum range of the wall stress. A region S enclosed by the one-dot chain lines and the two-dot chain lines, namely, a region S in which the optimum ranges of the shear stress and wall stress overlap each other indicates an optimum range of the healthy subject persons. If a point defined by the calculated values of the shear stress SS1 and wall stress WS is located within the above-indicated region S, the blood vessel function is diagnosed to be normal. If one of the calculated values of the shear stress SS1 and wall stress WS is outside the corresponding optimum range, on the other hand, the above-indicated point is located outside the region S, and the blood vessel function is diagnosed to be abnormal. Thus, the position of the point indicative of the result of calculation relative to the region S is indicated on the monitoring image display device 30, as a result of the diagnosis by the blood vessel function diagnosing portion 124, permitting easy diagnosis of the blood vessel function.

The display control portion 126 is provided with a memory portion in the form of a memory portion 128 for storing the results of calculation (shear stress SS1 and wall stress WS) of each subject person from time to time, and therefore stores the results of past calculation, so that the results of present calculation are displayed together with the results of the past calculation. Different marks are displayed for indicating the respective results, as indicated in FIG. 23, so that the results of the present calculation are distinguishable from the results of the past calculation. Further, arrow marks may be displayed to indicate the order of the results of calculation, for easier recognition of the chronological change of the results of calculation. In addition, where the number of the results of measurement is relatively large, different marks may be used for respective time periods of measurement, such a last time period of one month preceding the present moment of measurement, a time period of one month preceding the last time period, and a time period preceding the preceding time period.

By displaying the results of calculation in the past of the subject person as described above, it is possible to chronologically check the changes of the shear stress SS1 and wall stress WS, permitting a synthetic diagnosis for finding an adequate remedy and recognition of an effect of the remedy. For example, the adequate remedy, which differs depending upon which one of the shear stress SS1 and wall stress WS deviates from the corresponding optimum range or whether both of the shear stress and wall stress deviate from the respective optimum ranges, is selected depending upon those factors. Further, the effect of the remedy can be checked depending upon whether the parameter or parameters (shear stress SS1 and/or wall stress WS) which deviated from the corresponding optimum range is/are changing in a direction so as to fall back into the optimum range or not. Further, where one of the two parameters (wall stress WS or shear stress SS1) deviated from the optimum range, the adequate remedy and the effect of the remedy may be selected or checked on the basis of a change of the other parameter. Thus, the chronological display of the changes of the shear stress SS1 and wall stress WS permits regular monitoring of the state of deviation of the blood vessel function, making it possible to select the adequate remedy and to evaluate the effect of the remedy.

Figure 24:
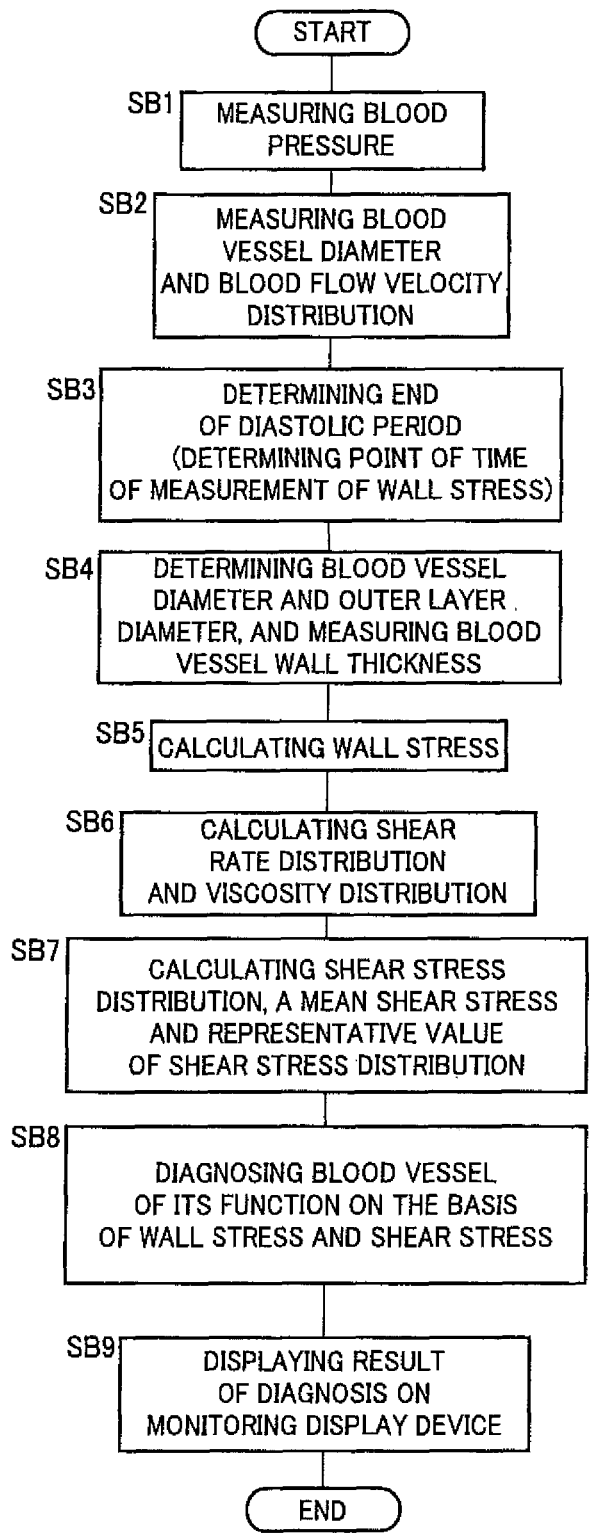
FIG. 24 is a flow chart illustrating major control operations of the blood vessel function inspecting apparatus (electronic control device) of FIG. 14, namely, control operations to implement the diagnosis of an abnormality of the blood vessel function on the basis of the shear stress and wall stress.

FIG. 24 is the flow chart illustrating major control operations of the blood vessel function inspecting apparatus 95 (electronic control device 28), namely, control operations to implement the diagnosis of the blood vessel function on the basis of the shear stress and wall stress.

Initially, step SB1 (hereinafter "step" being omitted) corresponding to the blood pressure measuring portion 94 is implemented to measure the blood pressure by pressurizing the cuff 21. Then, the control flow goes to SB2 corresponding to the blood vessel diameter measuring portion 80 and the blood flow velocity distribution measuring portion 100, to continuously measure and store the blood vessel diameter d1, the outer layer diameter d2 and the blood flow velocity distribution DS, a predetermined length of time (60-120 seconds, for example). Described more specifically, the position of the blood vessel 20 is determined by a tomographic image generated on the basis of scattered ultrasonic waves (reflected waves) received by the long-axis ultrasonic detector array C of the ultrasonic probe 24, and the blood vessel diameter d1 and the outer layer diameter d2 are measured. At the same time, a two-dimensional velocity vector distribution (blood flow velocity distribution DS) in a two-dimensional tomographic plane is measured. The measured diameters d1, d2 and velocity vector distribution are stored in memory from time to time. SB3 corresponding to the wall stress calculating portion 122 is then implemented to determine the end point of the diastolic period at which the wall stress WS is to be measured. This end point of the diastolic period is a point of time at which the blood vessel diameter d1 measured in SB2 a predetermined length of time (more than 60 seconds, for instance) after the moment of initiation of the measurement is minimized. The end point of the diastolic period is determined the predetermined length of time after the moment of initiation of the measurement, since the shear stress SS corresponding to the wall stress WS at the end point of the diastolic period is calculated on the basis of the blood flow velocity distribution DS prior to the end point of the diastolic period. After the end point of the diastolic period is determined in SB3, the control flow goes to SB4 corresponding to the blood vessel diameter measuring portion 80 and the blood vessel wall thickness measuring portion 84, to determine the blood vessel diameter d1 and outer layer diameter d2 measured at the end point of the diastolic period determined in SB3, as representative values during calculation of the wall stress on the basis of which the wall thickness t (d2−d1)/2) of the blood vessel 20 is calculated. In SB5 corresponding to the wall stress calculating portion 122, the wall stress WS of the blood vessel 20 at the end point of the diastolic period is calculated on the basis of the diastolic blood pressure DBP measured in SB1, and the blood vessel diameter d1 and wall thickness t determined in SB4. It will be understood that the SB4 and SB5 described above correspond to a major part of the wall stress calculating portion 98.

Then, SB6 corresponding to the shear rate distribution calculating portion 104 and the blood viscosity distribution calculating portion 102 is implemented to calculate the viscosity distribution DV within the blood vessel 20 at each point of measurement within the predetermined period of time corresponding to 20 heart beat pulses just prior to the reference point of time (in other words, the period of 20 heart beat pulses which terminates at the end of the reference point of time), which reference point of time is about 20-30 seconds (20-30 heart beat pulses) prior to the point of time of calculation of the wall stress WS. This calculation of the viscosity distribution DV is made on the basis of the measured flow velocity distribution DS at each point of measurement stored in the memory, and according to the two-dimensional Navier-Stokes equations stored in the memory. Also calculated in SB6 is the shear rate distribution DSR of the blood within the blood vessel 20 (blood shear rate distribution DSR) at each point of measurement within the predetermined period of time corresponding to 20 heart beat pulses prior to the reference point of time (the period of 20 heart eat pulses which terminates at the end of the reference point of time), which reference point of time is about 20-30 seconds (20-30 heart beat pulses) prior to the point of time of calculation of the wall stress WS. This calculation of the shear rate distribution DSR is made on the basis of the measured flow velocity distribution DS at each point of measurement stored in the memory.

SB7 corresponding to the shear stress distribution calculating portion 106 is then implemented to calculate the shear stress distribution DSS at each point of measurement corresponding to the 20 heart beat pulses, on the basis of the calculated viscosity distribution DV and shear rate distribution. DSR within the blood vessel 20 within the time period of 20 heart beat pulses prior to the reference point of time, and to calculate the mean value SS (shear stress SS) of the blood shear stress at each point of measurement within the time period of 20 heart beat pulses just prior to the reference point of time, on the basis of the calculated shear stress distribution DSS. Also calculated in SB7 as the representative value SS1 of the shear stress SS is one of an integral value of the above-described shear stress within the predetermined time period (corresponding to the 20 heart beat pulses) just prior to the referenced point of time, a mean value of the shear stress per one heart beat pulse within the predetermined time period, and an integral value or mean value of the instantaneous values in synchronization with the heart beat pulses within the predetermined time period, on the basis of the calculated shear stress SS corresponding to the 20 heart beat pulses prior to each point of measurement. It is noted that the above-described SB2, SB6 and SB7 correspond to a major part of the shear stress calculating portion 96.

In SB8 corresponding to the blood vessel function diagnosing portion 124, the blood vessel 20 is diagnosed of its abnormality of function on the basis of the wall stress WS and shear stress SS1 (representative value) calculated in SB4 and SB7. Described more specifically, SB8 is implemented to determine whether the wall stress WS is held within the predetermined optimum range (WShi-WSlo), and whether the shear stress SS1 is held within the predetermined optimum range (SShi-SSlo). If both of the wall stress WS and the shear stress SS1 are held within the respective optimum ranges, the blood vessel function is diagnosed to be normal. If at least one of the wall stress WS and the shear stress SS1 is outside the optimum range, on the other hand, the function of the blood vessel 20 is diagnosed to be abnormal.

In SB9 corresponding to the display control portion 126, the result of the diagnosis in SB8 is displayed on the monitoring image display device 30, in the form of a message, numerical values or a two-dimensional graph, to indicate whether the wall stress WS and the shear stress SS1 deviate from the optimum ranges. Described more specifically, the positional relationship of the point indicating the calculated wall stress WS and the shear stress SS1 with respect to the region S in which the optimum ranges of the wall stress WS and the shear stress SS1 overlap each other is displayed in the two-dimensional graph in which the wall stress WS and the shear stress SS1 are taken along the respective two axes. If the above-indicated point is located within the region S, the blood vessel function is recognized to be normal. If the point is outside the region S, on the other hand, the blood vessel function is recognized to be abnormal (to be in an unhealthy state). The results of the past measurements are also displayed to permit judgment regarding a change of the blood vessel function.

As described above, the present embodiment is provided with the blood vessel function diagnosing portion 124 configured to diagnose the blood vessel of its function, depending upon whether at least one of the calculated shear stress SS1 and wall stress WS is outside the corresponding one of the optimum ranges respectively predetermined for the shear stress and the wall stress. Thus, the blood vessel function can be easily diagnosed for any abnormality, by calculating the shear stress SS1 and the wall stress WS. The blood vessel 20 has a compensating function to always hold the shear stress SS1 and the wall stress WS within the optimum ranges, irrespective of variations of the blood flow and blood pressure. If the wall stress WS increases with a rise of the blood pressure, for example, the wall thickness t of the blood vessel 20 increases to hold the wall stress WS constant. If the shear stress SS1 increases with an increase of the blood viscosity $\mu$, for example, the blood vessel diameter d1 increases to reduce the shear rate for holding the shear stress SS1 constant. Thus, the shear stress SS1 and wall stress WS are kept normal owing to the compensating function of the blood vessel 20. If this compensating function is lost, the shear stress SS1 and wall stress WS deviate from the above-indicated optimum ranges. Accordingly, the diagnosis as to whether the above-indicated compensating function of the blood vessel 20 is normal can be accurately implemented by determining from time to time whether the calculated shear stress SS1 and wall stress WS have deviated from the optimum ranges. If at least one of the shear stress SS1 and wall stress WS is outside the optimum range, for instance, a chronological change of the deviation from the optimum range is monitored from time to time, to synthetically find a cause and an adequate remedy for the deviation, and also an effect of the remedy. The loss of the compensating function is considered to cause arteriosclerosis, so that the present blood vessel inspecting apparatus can be utilized as means for early discovery of the arteriosclerosis.

The blood vessel function inspecting apparatus according to the present embodiment further comprises the monitoring image display device 30 configured to display the relationship between the calculated shear stress SS1 and wall stress WS, in the two-dimensional graph, and the display device 30 displays the region S in which the above-described optimum ranges of the shear stress SS1 and wall stress WS overlap each other, and indicates the position of the point (calculated result) indicative of the relationship between the calculated shear stress SS1 and wall stress WS relative to the above-described region S. Since the position of the point indicative of the relationship between the shear stress SS1 and the wall stress WS relative to the region S is displayed, the diagnosis as to whether the blood vessel function is normal or not can be easily implemented on the basis of the relative position between the above-indicated point and the region S. Described more specifically, the blood vessel function can be easily diagnosed to be normal if the point is held within the region S, and to be abnormal if the point is outside the region S.

The blood vessel function inspecting apparatus according to the present embodiment further comprises the memory portion 128 for successively storing the shear stress SS1 calculated by the shear stress calculating portion 96, and the wall stress WS calculated by the wall stress calculating portion 98, and the monitoring image display device 30 indicates the results of the present calculation of the shear stress SS1 and wall stress WS, together with the results of the past calculation of the shear stress SS1 and wall stress WS stored in the memory portion 128, such that the results of the present calculation are distinguishable from the results of the past calculation. Thus, it is possible to compare the results of the present calculation with the results of the past calculation, and to check a chronological change of the blood vessel function. Accordingly, if one of the shear stress SS1 and the wall stress WS has deviated from the optimum range, the adequate remedy for the deviation and the effect of the remedy can be found and evaluated depending upon whether the shear stress SS1 or wall stress WS is changing in a direction toward the optimum range.

In the present embodiment, the shear stress SS1 is one of: an integral value of the shear stress SS1 within the predetermined period of time preceding the reference point of time which is prior to the present point of time by the predetermined length of time corresponding to the delay of the response of a change of the wall stress WS which takes place with a change of the shear stress SS (within the predetermined period of time of 20 heart beat pulses); a mean value of the shear stress per one heart beat pulse within the predetermined period of time; and an integral or mean value of instantaneous values of the shear stress measured in synchronization with the respective heart beat pulses within the predetermined period of time. It is generally known that the endothelial skin of the blood vessel 20 instantaneously responds to a change of the blood flow, but there exists a response time delay from the moment of production of nitrogen monoxide NO to the moment at which the smooth muscles are relaxed due to exposure to the nitrogen monoxide NO which has diffused through the inner layer and reached the smooth muscles. That is, the time-delay occurs between the change of the shear stress and the change of the wall stress. In view of this response time delay, the representative value of the shear stress SS1 used for the diagnosis of the blood vessel function is calculated on the basis of the shear stress values at the respective points of measurement within the predetermined period of time preceding the reference point of time which is prior to the present point of time of calculation of the wall stress by the length of time corresponding to the response time delay, so that the blood vessel can be diagnosed of its function on the basis of the shear stress SS1 and wall stress WS which have a correlation with each other. It is also noted that the representative value of the shear stress SS1 used for the diagnosis of the blood vessel function is not an instantaneous value at a given point of time (e.g., at the reference point of time), but is calculated on the basis of the values of the shear stress SS at the respective points of time within the predetermined period of time (of 20 heart beat pulses) which terminates at the reference point of time, so that the blood vessel can be diagnosed of its function on the basis of the shear stress SS1 which reflects the stimuli regularly acting on the blood vessel wall.

The present embodiment is further configured such that the shear stress SS is calculated on the basis of the blood flow velocity distribution DS and according to the stored two-dimensional or three-dimensional Navier-Stokes equations. Accordingly, the shear stress SS is accurately calculated so that the blood vessel function inspecting apparatus 95 is practically operable.

The present embodiment is further configured such that the wall stress WS is calculated on the basis of the diastolic blood pressure DBP, the blood vessel diameter d1 and the wall thickness t of the blood vessel 20. Accordingly, the wall stress WS is accurately calculated by measuring the diastolic blood pressure DBP, blood vessel diameter d1 and wall thickness t, so that the blood vessel function inspecting apparatus 95 is practically operable.

The present embodiment is further configured such that the ultrasonic probe 24 which irradiates the ultrasonic waves toward the blood vessel 20 is provided with the long-axis ultrasonic detector array C having a plurality of ultrasonic oscillators arranged linearly in the longitudinal direction (direction of the y axis) of the blood vessel 20, and the first short-axis ultrasonic detector array A and the second short-axis ultrasonic detector array B each of which has a plurality of ultrasonic oscillators linearly arranged in the direction perpendicular to the longitudinal direction of the blood vessel 20, and the blood flow velocity distribution DS is measured with the ultrasonic waves irradiated from the long-axis ultrasonic detector array C, and the ratio of change of the blood vessel diameter is measured with the ultrasonic waves irradiated from the first short-axis ultrasonic detector array A. Accordingly, it is possible to implement the measurement of the above-described blood flow velocity distribution DS and the measurement of the ratio of change of the diameter of the above-described blood vessel 20, concurrently with each other, by using the practically operable ultrasonic probe 24.

Embodiment 3

Figure 25:
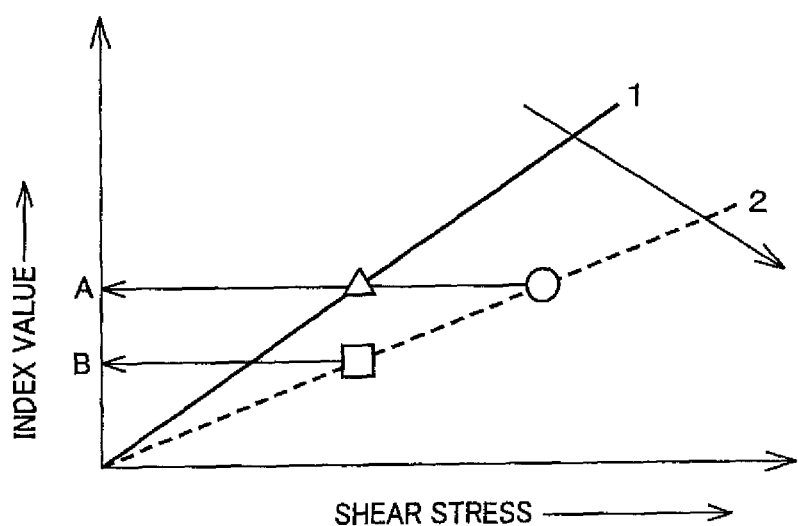
FIG. 25 is a view showing a change of data obtained by standardizing the index values by the shear stress.

The function index value X1 and function/organic index value X3 in the preceding embodiments may be standardized by the above-described shear stress SS, to improve the accuracy of the blood vessel evaluation on the basis of the index values. FIG. 25 is the view showing a change of data obtained by standardizing the index values by the shear stress SS. For instance, an index value represented by a mark "Δ" and lying on a solid line 1 and an index value represented by a mark "o" and lying on a broken line 2 are both equal to a value A, at different values of the shear stress SS. Accordingly, the accuracy of evaluation on the basis of measurement data can be improved by standardizing the index value by the shear stress SS, namely, by converting the index value into a value at the same value of the shear stress SS. For example, in FIG. 25, the index value represented by the mark "o" and lying on the broken line 2 is standardized by the shear stress SS corresponding to the index value represented by the mark "Δ" and lying on the solid line 1, into the index value represented by a mark "□". Namely, the index value A standardized by the shear stress SS is converted into an index value B. The accuracy of evaluation can be improved by standardizing the index value by the shear stress SS as described above.

As described above, the present embodiment is configured such that each of the above-described index values is standardized by the shear stress SS, so that each index value is compensated by the shear stress SS, so as to reduce a degree of variation of the measurement data, for further improving the accuracy of diagnosis of the blood vessel function. That is, the variation of the index value due to a difference of the shear stress SS is eliminated, to further improve the accuracy of evaluation on the basis of the index value.

While the embodiments of this invention have been described above by reference to the drawings, for illustrative purpose only, it is to be understood the present invention may be otherwise embodied.

For example, the first illustrated embodiment is configured to calculate the function index value X1, organic index value X2 and function/organic index value X3 on the basis of the maximum value Rmax as the representative value of the dilatation amount R, and the blood vessel diameter d1 and wall thickness t measured upon measurement of the maximum value Rmax as the representative values. However, the time point at which the maximum value Rmax is measured need not be the reference point, and may be replaced by a mean value of the dilatation value R within a predetermined time period just after the moment of releasing of the blood vessel from the blood flow obstruction.

In the illustrated embodiment, the wall thickness t is defined as a difference [$=(d2-d1)/2$] between the outside diameter d2 of the outer layer La of the blood vessel 20, and the blood vessel diameter d1 which is the inside diameter of the inner layer $L_1$. However, the wall thickness t may be defined as a difference [=(d3−d1)/2] between the outside diameter d3 of the intermediate layer $L_2$ shown in FIG. 3 (inside diameter d3 of the outer layer $L_3$) and the blood vessel diameter d1. In other words, the wall thickness t may be defined as a sum of the thickness of the inner layer $L_1$ and the thickness of the intermediate layer $L_2$.

While the illustrated embodiment is configured to display the relationship between the function index value X1 and the organic index value X2 on the monitoring image display device 30, the embodiment may be modified to further display the relationship of FIG. 10 between the function/organic index value X3 and the age, and the relationship of FIG. 12 between the function index value X1 and the age. In this case, the evaluation of the blood vessel function of the subject person may be facilitated by further displaying an optimum value corresponding to the age of the subject person.

Although the second illustrated embodiment uses the shear stress SS as one index value for diagnosing the blood vessel of its function, the shear rate SR (mean value thereof) may be used in place of the shear stress SS, for diagnosing the blood vessel for any abnormality, since the blood viscosity μ of the same subject person, for example, is kept unchanged.

While the shear stress SS is calculated according to the two-dimensional Navier-Stokes equations in the illustrated embodiment, the shear stress SS may be calculated according to general arithmetic equations well known in the art.

In the second illustrated embodiment, the wall stress WS is used as one index value for diagnosing the blood vessel of its function. However, the wall stress WS may be replaced by a wall-stress-related value corresponding to the wall stress WS one-to-one, such as a ratio of a wall tensile force or the wall thickness t of the blood vessel 20 to the blood vessel diameter d1, for diagnosing the blood vessel for any abnormality. In view of a fact that the diagnosis of the blood vessel for any abnormality on the basis of this alternative parameter is substantially identical with the diagnosis on the basis of the wall stress WS, it is to be understood that the term "wall stress SS" is interpreted to comprehend the wall-stress-related value described above.

In the illustrated embodiment, the wall stress WS is calculated at the reference point of time which is the end point of the diastolic period. However, the reference point of time need not be limited to the end point of the diastolic period (point of time at which the blood pressure is lowest), and may alternatively be a point of time within the systolic period, at which the blood flow velocity is highest (at which the blood pressure is highest).

Although the illustrated embodiment of the flow chart of FIG. 24 is configured to calculate the shear stress SS after calculation of the wall stress WS, these shear stress SS and wall stress WS are actually calculated at substantially the same time. In this respect, the order of calculation of these parameters may be suitably changed without departing from the principle of this invention.

In the illustrated embodiment, the wall stress calculating portion 98 is operated to calculate the wall stress WS immediately after the determination of the end point of the diastolic period. However, the wall stress calculating portion 98 may calculate the wall stress WS a predetermined length of time after temporarily storing information necessary for calculating the wall stress WS, such as the blood vessel diameter d1 and wall thickness t measured at the end point of the diastolic period.

In the illustrated embodiment, the end point of the diastolic period is determined as the point of time at which the blood vessel diameter d1 is minimized. However, the end point of the diastolic period may be determined as a point of time at which the detected pulse wave has the lower peak amplitude, or as a point of time at which the R wave of an ECG (electrocardiogram) is detected.

It is to be understood that the present invention may be embodied with various other changes not illustrated herein, without departing from the spirit of this invention.

NOMENCLATURE OF REFERENCE SIGNS

10: Sensor holder 12: Hybrid probe unit 14: Live body 16: Brachium 18: Skin 20: Blood vessel 22, 95: Blood vessel function inspecting apparatus 23: Pressure sensor 24: Ultrasonic probe 25: Pump 26: Multi-axes drive device 27: Detection plane 28: Electronic control device 29: Pressure control valve 30: Monitoring image display device (Display device) 32: Ultrasonic wave drive control circuit 34: 3-axes drive motor control circuit 36: Magnet stand 38: Unit fixture 42: End portions 44: Connecting member 45: Connecting member 46: Link 47: Link 48: Engaging holes 50: Universal joint portion 51: Universal joint portion 52: Fixing knob 54: Pivotal joint portion 72: Echo receiving portion
80: Blood vessel diameter measuring portion 82: Blood vessel dilatation amount measuring portion 84: Blood vessel wall thickness measuring portion 86: Blood vessel function index value calculating portion 88, 124: Blood vessel function diagnosing portion 90, 126: Display control portion 92, 128: Memory portion 94: Cuff pressure control portion 95: Blood pressure measuring portion 96: Shear stress calculating portion 98: Wall stress calculating portion 100: Blood flow velocity distribution measuring portion 102: Blood viscosity distribution calculating portion 104: Shear rate distribution calculating portion 106: Shear stress distribution calculating portion 122: Wall stress calculating portion 130: Sub-regions.

The invention claimed is:

1. A blood vessel function inspecting apparatus comprising:
   an ultrasonic probe configured to irradiate ultrasonic waves toward a blood vessel within a live body through a skin and detect reflected ultrasonic signals;
   a processer having a program stored therein for causing the processor to perform executable portions, the executable portions comprising:
      a shear stress calculating portion configured to calculate a shear stress of blood within a blood vessel;
      a wall stress calculating portion configured to calculate a wall stress of said blood vessel; and
      a blood vessel function diagnosing portion configured to diagnose the blood vessel of its abnormality of function, depending upon whether at least one of the calculated shear stress and wall stress is outside a corresponding one of optimum ranges respectively predetermined for said shear stress and said wall stress; and
   a display device configured to display a relationship between the calculated shear stress and wall stress, in a two-dimensional graph,
   wherein the display device is configured to display a region in which said optimum ranges of said shear stress and wall stress overlap each other, and indicate a position of a calculation result indicative of the relationship between the calculated shear stress and wall stress relative to said region.

2. The blood vessel function inspecting apparatus according to claim 1, the processor further comprising a memory portion configured to store the shear stress calculated by said shear stress calculating portion, and the wall stress calculated by said wall stress calculating portion successively, and wherein said display device is configured to indicate results of present calculation of said shear stress and wall stress, together with results of past calculation of said shear stress and wall stress stored in said memory portion, such that the results of the present calculation are distinguishable from the results of the past calculation.

3. The blood vessel function inspecting apparatus according to claim 1, wherein said shear stress is one of an integral value of said shear stress within a predetermined period of time preceding a reference point of time which is prior to a present point of time by a predetermined length of time corresponding to a delay of a response of a change of said wall stress which takes place with a change of said shear stress;

a mean value of the shear stress per one heart beat pulse within said predetermined period of time; and an integral or mean value of instantaneous values of the shear stress measured in synchronization with the respective heart beat pulses within said predetermined period of time.

4. The blood vessel function inspecting apparatus according to claim 1, wherein said shear stress calculating portion is configured to calculate said shear stress on the basis of a flow velocity distribution of said blood and according to stored two-dimensional or three-dimensional Navier-Stokes equations.

5. The blood vessel function inspecting apparatus according to claim 1, wherein said wall stress calculating portion is configured to calculate said wall stress on the basis of a blood pressure, a diameter and a wall thickness of said blood vessel.

6. A blood vessel function inspecting apparatus comprising:
an ultrasonic probe configured to irradiate ultrasonic waves toward a blood vessel within a live body through a skin and detect reflected ultrasonic signals;
a processer having a program stored therein for causing the processor to perform executable portions, the executable portions comprising:
a shear stress calculating portion configured to calculate a shear stress of blood within a blood vessel;
a wall stress calculating portion configured to calculate a wall stress of said blood vessel; and
a display device configured to display a relationship between the calculated shear stress and wall stress, in a two-dimensional graph,
and wherein the display device is configured to display a region in which optimum ranges of said shear stress and wall stress overlap each other, and indicate a position of a calculated result indicative of the relationship between the calculated shear stress and wall stress relative to said region.

* * * * *